United States Patent [19]
Yarush et al.

[11] Patent Number: 5,879,289
[45] Date of Patent: Mar. 9, 1999

[54] HAND-HELD PORTABLE ENDOSCOPIC CAMERA

[75] Inventors: Don Yarush, Henderson; Martin G. Sosa; Gary Handelin, both of Carson City, all of Nev.

[73] Assignee: Universal Technologies International, Inc., Las Vegas, Nev.

[21] Appl. No.: 680,174

[22] Filed: Jul. 15, 1996

[51] Int. Cl.⁶ .............................. A61B 1/04; A61B 1/07
[52] U.S. Cl. ..................... 600/179; 600/109; 600/127; 600/130; 600/131; 600/167; 600/182
[58] Field of Search ................... 600/109, 127, 600/131, 160, 167, 179, 199, 200, 182, 178, 452, 558; 348/65, 66, 70, 71, 77, 79, 80, 158, 333, 370, 372, 373, 376; 433/29; 359/385, 389, 387; 362/32; 385/117, 119

[56] References Cited

U.S. PATENT DOCUMENTS

| | | |
|---|---|---|
| 3,638,643 | 2/1972 | Hotchkiss . |
| 4,580,198 | 4/1986 | Zinnanti, Jr. . |
| 4,602,281 | 7/1986 | Nagasaki et al. ........................ 600/180 |
| 4,633,304 | 12/1986 | Nagasaki ................................. 600/109 |
| 4,651,202 | 3/1987 | Arakawa . |
| 4,685,452 | 8/1987 | Riester ................................... 600/200 |
| 4,727,859 | 3/1988 | Lia .......................................... 600/175 |
| 4,736,734 | 4/1988 | Matsuura et al. ........................ 600/178 |
| 4,742,819 | 5/1988 | George . |
| 4,756,304 | 7/1988 | Watanabe . |
| 4,807,594 | 2/1989 | Chatenever . |
| 4,844,071 | 7/1989 | Chen et al. . |
| 4,851,866 | 7/1989 | Ciarlei et al. . |
| 4,883,061 | 11/1989 | Zeimer ................................... 600/452 |
| 4,895,138 | 1/1990 | Yabe ....................................... 600/179 |
| 4,905,670 | 3/1990 | Adair ..................................... 600/104 |
| 4,979,498 | 12/1990 | Oneda et al. . |
| 5,042,915 | 8/1991 | Akutsu et al. . |
| 5,083,059 | 1/1992 | Giraham et al. . |
| 5,117,154 | 5/1992 | Thomas et al. . |
| 5,125,394 | 6/1992 | Chatenever et al. . |
| 5,138,228 | 8/1992 | Thomas et al. . |
| 5,144,201 | 9/1992 | Graham et al. . |
| 5,314,070 | 5/1994 | Ciarlei ................................... 206/570 |
| 5,363,838 | 11/1994 | George . |
| 5,363,839 | 11/1994 | Lankford . |
| 5,498,230 | 3/1996 | Adair ..................................... 600/112 |
| 5,523,786 | 6/1996 | Parulski ................................. 348/70 |
| 5,527,261 | 6/1996 | Monroe et al. . |
| 5,575,757 | 11/1996 | Kennedy et al. ....................... 600/167 |

FOREIGN PATENT DOCUMENTS

| | | |
|---|---|---|
| 891888 | 12/1993 | Australia . |
| 0 573 158 A1 | 12/1993 | European Pat. Off. . |
| 2 695 785 | 9/1992 | France ..................................... 5/28 |
| 94 05 345.6 | 9/1994 | Germany . |
| 273473 | 7/1927 | United Kingdom . |
| 9315648 | 8/1993 | WIPO .................................. 600/160 |

OTHER PUBLICATIONS

EarCrafters, Inc. Introduces the Most "User Friendly" Portable S–Video Otoscope on the Market, *The Hearing Journal,* vol. 47, No. 12, Dec. 1994.

Cudal® Products Corp. Distributor Price Information Brochure, Sep. 1995.

*Primary Examiner*—John P. Leubecker
*Attorney, Agent, or Firm*—Workman, Nydegger & Seeley

[57] ABSTRACT

A portable, hand-held endoscopic camera having all of the necessary components for performing endoscopic procedures comprises power source means, lens means, light source means, and video camera means. The portable endoscopic camera is adaptable to a wide variety of systems and includes a highly efficient means for focusing the illumination of the light source. The lens means includes a fiber bundle and the light source means includes a bulb. The bulb is positioned in an abutting relationship with the fiber bundle, thereby focusing light into the fiber bundle. The camera is selectively operable in a cordless and cord-operated mode.

37 Claims, 10 Drawing Sheets

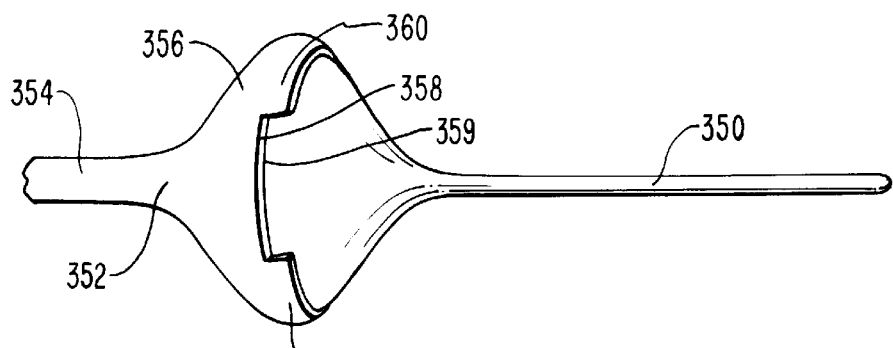
FIG. 13
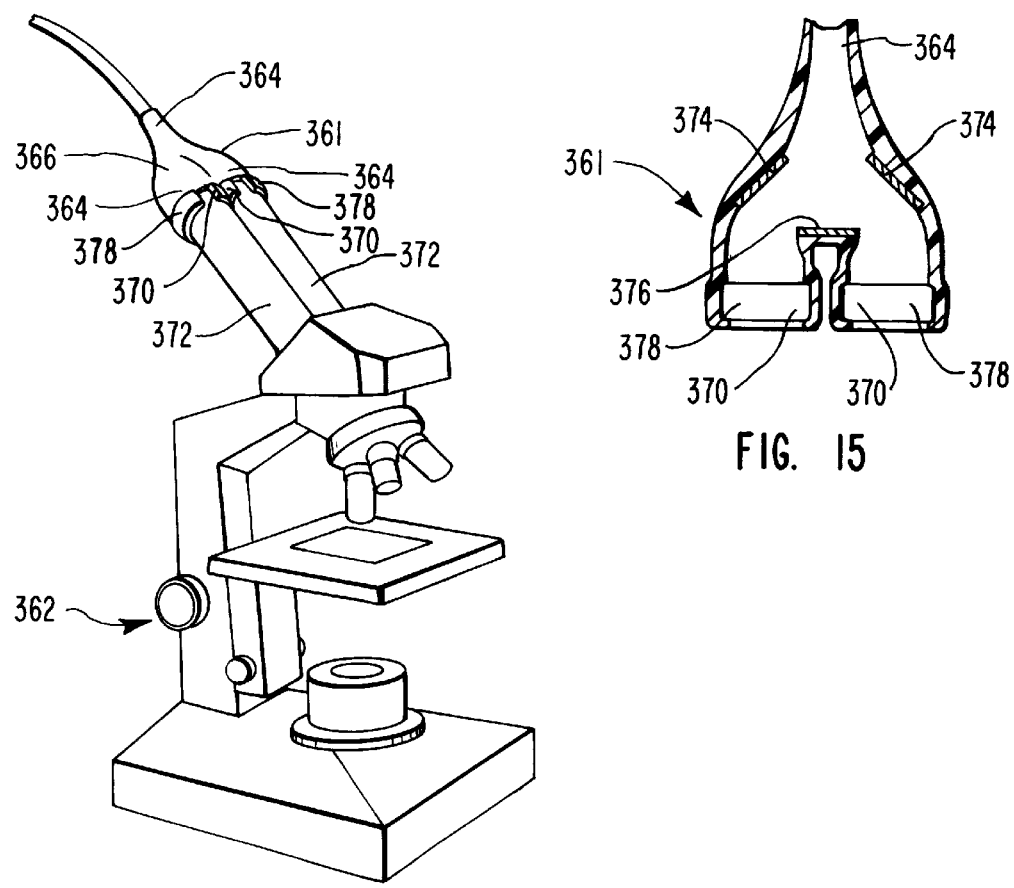
FIG. 14
FIG. 15

HAND-HELD PORTABLE ENDOSCOPIC CAMERA

BACKGROUND OF THE INVENTION

1. The Field of the Invention

This invention relates to endoscopic cameras and more particularly, to a portable, hand-held endoscopic camera.

2. Background

The field of endoscopy has greatly enhanced a practitioner's ability to penetrate objects to view internal mechanisms and other features with minimal intrusion. Endoscopes have broad reaching application in the field of diagnostic and therapeutic medicine, surgery, dentistry, computer inspection, customs inspection, plumbing, mining, automobile mechanics, veterinary medicine, aviation, remote control devices, safety equipment, monitoring devices, police investigations and in a variety of other settings in which detailed inspection is desired.

A major challenge facing the field of endoscopy is the vast amount of equipment typically required. The equipment found in the prior art typically includes a large monitor, a light source, a power source and an endoscope. In addition, fiber optic and power cables are required to connect the monitor, light source, and power source to the endoscope. Typical such equipment is often permanently or semi-permanently installed in a tightly enclosed area, such as a dental office. Offices must typically be specially adapted to accommodate the cumbersome equipment, requiring expensive wiring of circuitry and the placement of plugs and cables within the room. Each individual room in a clinic is required to maintain the equipment and wiring.

Compounding the problem, the optic and power cables connecting the light source, power source and monitor to the endoscope are cumbersome to use. The cables must be dragged around the area to be viewed, wrapping them around the patient's body and objects within the room to look inside an ear or mouth, for example. Fiber optic cable is a rather stiff and inflexible glass cable which can be easily broken during such procedures. As the cables are flexed, the fiber optics may be broken. As the glass is broken, the image received is distorted and distortions known as "ghosts" appear on the monitor.

Generally, the longer the fiber optic cable employed in a particular procedure, the more light is needed. Typical light sources require high voltages, preventing use of battery operated systems.

The use of high intensity light sources also creates an inefficient use of space. The light source employed in many endoscopic systems is a large bulb, such as a halogen bulb, which generates a considerable amount of heat typically in the range of about 50 to 150 watts. When employed near a probe which is placed in a body cavity, the typical light source tends to heat the probe, which is uncomfortable or dangerous to sensitive body openings such as an ear. As a result, many light sources consist of a separate component having a large enclosure for housing the light source. A fan may be used to cool the light source or the connections thereto, creating an exhaust system, but also requiring additional energy and more space. Other systems employ a heat sink or shield to buffer the heat, which also requires increased amounts of space.

An additional drawback to endoscopic technology typically found in the prior art is the requirement that the practitioner view a monitor which is located away from the patient or object under inspection. This often requires the physician to attempt to aim the endoscope at a precise, enclosed location while looking in a completely different direction, which is often difficult and cumbersome. In addition, typically if the practitioner desires to employ a different type of probe, the practitioner must often employ a different endoscope.

In addition, typical cord operated systems are not readily used in countries foreign to the United States. For example, typical endoscopic systems fail to readily convert to 220 volt, 50 cycle power sources which are commonly used in countries foreign to the United States, requiring the practitioner to employ a cumbersome transformer when travelling to a foreign country.

SUMMARY AND OBJECTS OF THE INVENTION

In response to this tremendous need in the art, the present invention provides a hand-held, portable endoscopic camera which is selectively operable in a cordless and a cord-operated mode. The portable endoscopic camera of the present invention is compatible with a variety of output systems, light requirements, adapters, and probes but does not rely on bulky fiber optic cables connecting the endoscope to the other equipment. The portable endoscopic camera features a light source which is capable of illuminating the endoscope, yet, at the same time is small enough that it does not rely on fans or heat sinks to prevent overheating. The endoscopic camera contains all of the necessary equipment required to perform endoscopic procedures in a single, hand-held housing.

The hand-held, portable endoscopic camera includes a lens system having dual roles. First, the lens system illuminates an object under examination through a fiber bundle that couples light from the light source means to the object. Second, the lens system translates an image of the illuminated object into video imaging circuitry which includes a charge coupled device ("CCD") array. A coupler optically couples the lens system to the video imaging circuitry. The video imaging circuitry converts the image of the object into video signals. The video imaging circuitry then outputs the video signals to a monitor. The practitioner then views the illuminated object on the video monitor.

In order to illuminate the object, the lens system includes a fiber bundle that channels the light from the light source means to the object under examination. A power supply supplies electrical power both to the light source and to the video imaging circuitry. In one embodiment, a housing houses the lens system, video imaging circuitry, light source and power supply. This self-contained unit allows the practitioner to inspect a variety of objects without using cumbersome cords and cables. As will be discussed in detail, a variety of additional components are connected to or mounted integrally within the hand-held housing.

In one embodiment, a display monitor is integral with the hand-held, portable apparatus, allowing the practitioner to look in generally the same direction while orienting the camera and viewing the object under inspection. In another embodiment, the hand-held, portable endoscopic camera is capable of sending a signal to a monitor configured to receive signals up to about 300 feet away. Thus, rather than placing an endoscope in every room of a clinic, for example, a single unit can be used in a variety of rooms and can send transmissions to a centralized monitor for video capture, recording, and viewing.

The endoscopic camera is adapted to receive a variety of adapters and probes, depending upon the desired procedure.

Since a change in procedure is often accompanied by a variation in light intensity, the disclosed camera is capable of delivering a variable light intensity for different types of fiber optic probes which may be employed.

If battery use and rechargeability is not desired on a certain occasion, it is possible to plug the hand-held, portable unit into an electrical outlet. In addition, it is possible to connect the hand-held, portable apparatus into a separate monitor, such as a wall or shelf mounted monitor. The hand-held unit is compatible with S-VHS and/or composite video output formats.

It is, therefore, an object of the invention to provide a portable endoscopic camera.

Another important object of the invention is to provide a portable, hand-held endoscopic camera that is self-contained, light-weight, and easy for a medical practitioner to manipulate.

It is a further object of the invention to provide a portable, hand-held endoscopic camera which features a lighting system capable of high-intensity illumination without creating an over abundance of heat.

It is a further object of the invention to provide a hand-held, portable endoscopic camera which is operable in a cordless and a cord-operated mode.

It is a further object of the invention to provide a hand-held portable endoscopic camera having a variety of capabilities, including various video output capabilities, various power source capabilities, adjustable light sources, transmitting features, memory features, and adaptability to a variety of probes and adapters and a variety of existing endoscopic systems.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawing depict only a typical embodiment of the invention and are not therefore to be considered to be limiting of its scope, the invention will be described and explained with additional specificity and detail through the use of the accompanying drawings in which:

FIG. 13 is a perspective view of a coupler for coupling the lens tube to a funnel shaped probe.

FIG. 14 demonstrates a coupler used to adapt a portable endoscopic camera to a microscope.

FIG. 15 is a cross-sectional view of the coupler of FIG. 14.

DETAILED DESCRIPTION OF THE PREFERRED EMBODIMENTS

Figure 1:
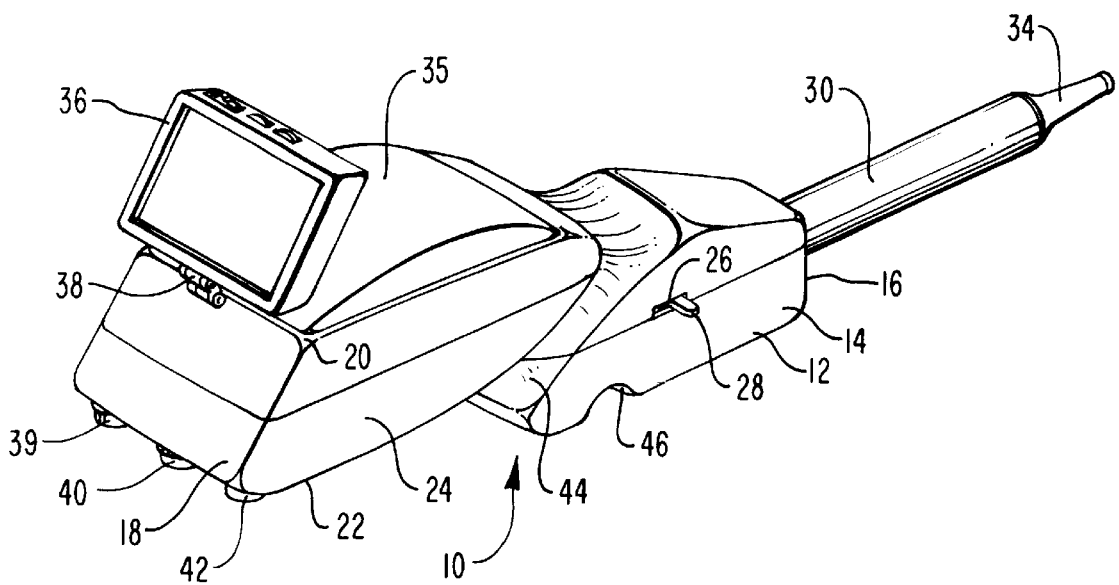
FIG. 1 is a perspective view of one embodiment of a portable endoscopic camera.

The headings contained in this application are for convenience of reference only and are neither intended, nor should they be construed, to be limiting in any respect.

A. Overview

The present invention provides a portable, self-contained endoscopic camera. The present invention is lightweight and is configured to rest comfortably in the hand of a medical professional or other user. The endoscopic camera of the present invention contains all of the necessary components required to perform endoscopic procedures in a single, hand-held unit. The present invention features an on-board, variable intensity light source for illuminating the objects to be viewed with the endoscopic camera, video camera circuitry for converting optical images into video signals, and a lens system that translates images to the optical input of the video camera. As discussed in more detail below, the present invention converts optical images captured at the input end of the lens systems into video signals, which can then be recorded or viewed on either a video monitor that is integral to the hand-held unit or to an external video monitor or other output device. The present invention may also include an RF transmitter so that the resulting video signals can be transmitted, via radio frequency signals, to a remote RF receiver coupled to a video monitor or other output device. The endoscopic camera is adapted to receive a variety of adapters and probes, depending upon the desired procedure.

The hand-held portable endoscopic camera of the present invention includes a lens means for (i) emitting light translated from a light source means through a fiber bundle to illuminate an object positioned adjacent the lens means; and (ii) for translating an image of the object from the lens means to the video imaging means. A coupling means optically couples the lens means to a video imaging means. The video imaging means converts the image of the object into video signals. The video imaging means then outputs the video signals to a display means where the practitioner views the illuminated object.

Also as discussed in detail below, a power supply means supplies electrical power both to the light source means, the video imaging means, the display means, and optionally, to a transmitter means. In one embodiment, a self-contained hand-held housing means houses the lens means, video imaging means, light source means, power supply means, and optionally, additional components including the display means, and/or transmitter means, such that the camera is convenient to manipulate. This self-contained housing means allows the practitioner to inspect a variety of objects without using cumbersome cords and cables. As will be discussed in detail, a variety of additional components are connected to or mounted integrally within the hand-held housing means.

The lens means will first be described in detail, after which the light source means will be described. The video imaging means is then described, followed by the power supply means. Various additional components will then be discussed, including the display means, transmitter means, and housing means.

B. The Lens System

With reference now to FIGS. 1–4, one presently preferred embodiment of the invention is the self contained. hand-held, portable endoscopic camera 10. As will be discussed in detail below, camera 10 contains all of the elements necessary for a practitioner, with a single hand, to orient a probe means in a patient's ear for example, and view the contents of the ear in a display means without cumbersome use of external cables. All of this is accomplished without having to look a significant distance away from the ear in order to view the display means and without being limited to a certain office or space. The practitioner is free to move about the patient, or to a different office, and is able to use the practitioner's free hand to otherwise assist in the procedure.

Figure 3:
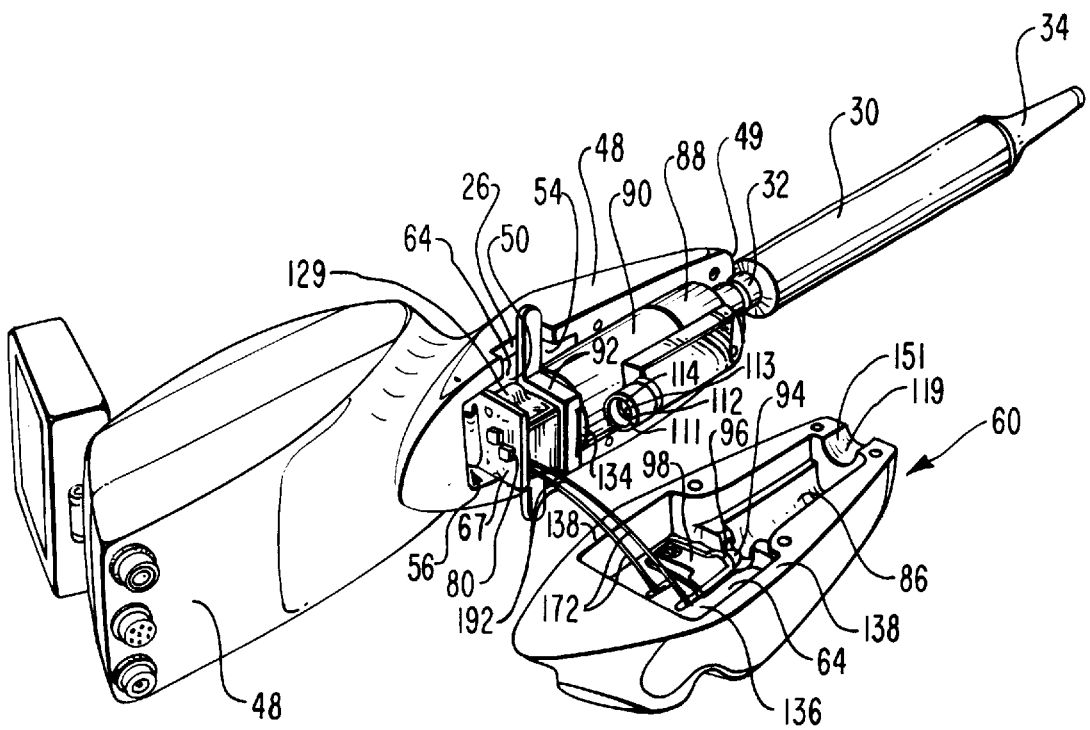
FIG. 3 is a perspective view of the portable endoscopic camera of FIG. 1 with the bottom of the camera housing removed.
Figure 4:
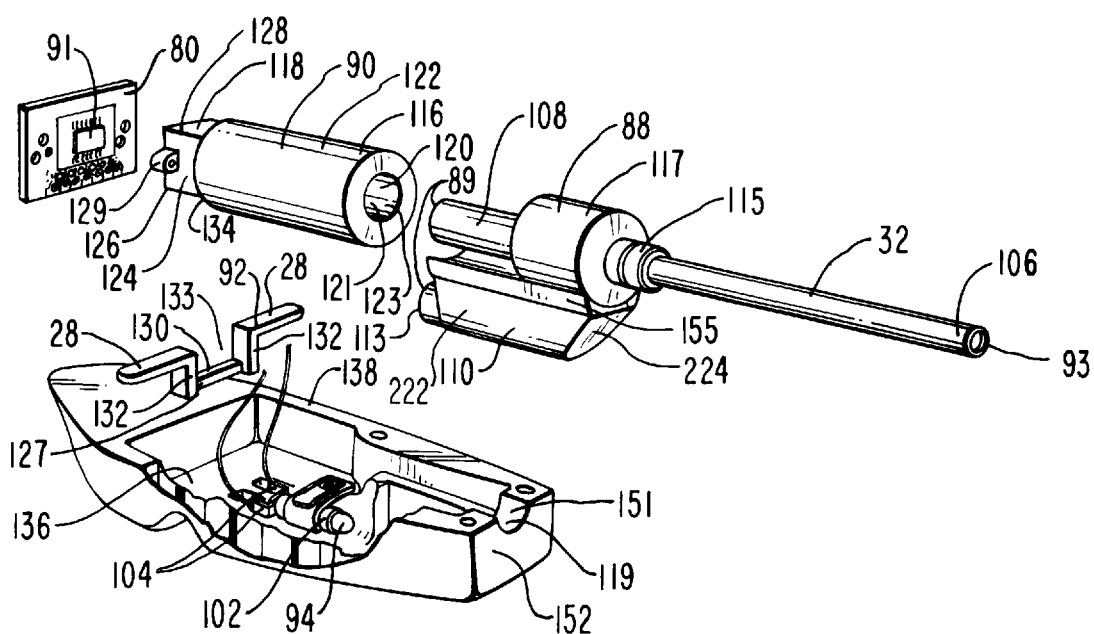
FIG. 4 is an exploded view of various components of the portable endoscopic camera of FIG. 1.

With reference now to FIGS. 3–4, in one embodiment, the lens means of camera 10 is comprised of a lens fiber module 88 having a proximal end 89 and a distal end 106. Module 88 is comprised of lens tube 32, lens tube 32 having a distal end 93, and a proximal portion 108. Module 88 further includes a distal hub 115 and a proximal hub 117. A fiber light input port 110 on proximal end 89 of module 88 houses a fiber bundle 112. Fiber light input port 110 includes a proximally extending cylindrical collar 113 adjacent fiber bundle 112. The inner diameter of collar 113 is the same or slightly larger than the outer diameter of fiber bundle 112. Collar 113 includes a proximal edge 111, the proximal edge 111 of collar 113 defining a proximal input port face 114.

Upon entering lens tube 32 from input port 110, fiber bundle 112 disperses into fibers along the longitudinal axis of lens tube 32. As will be discussed in detail below, input port 110 is optically coupled to the light source means for translating light from the light source means to the distal end of the lens tube 32. Light from the light source means travels into input port 110 and through the fibers in lens tube 32 to distal end 93 of lens tube 32 where the translated light is emitted from distal end 93, illuminating an object when distal end 32 is positioned adjacent the object. As will be discussed in further detail below, proximal portion 108 of lens tube 32 is optically coupled to the video imaging means for translating an image of the illuminated object from the distal end 93 of the lens tube 32 to the video imaging means.

By way of example, in one embodiment the preferred lens fiber module 88 is the lens fiber module of endoscopic assembly M-150 manufactured by Cuda Products Corporation, Jacksonville, Fla. The efficiency of module 88 is improved by polishing the finish of fiber bundle 112.

C. The Light Source

As indicated above, the lens means is optically coupled at its proximal end to the light source means. The purpose of the light source means is for producing light for illumination of the object. A variety of examples of light source means may be employed in the present invention. In one embodiment, a miniature incandescent lamp or other bulb is disposed within the same housing means in which the lens means is disposed. In another embodiment, a bulb is employed external to the housing means. In yet another embodiment, a light source means, such as a halogen bulb or other bulb, is enclosed within a separate lighting enclosure connected by a cable to the lens means. In another embodiment, the external light source means is enclosed within a supplemental casing means, such as the belt-mounted housing discussed below.

Figure 5:
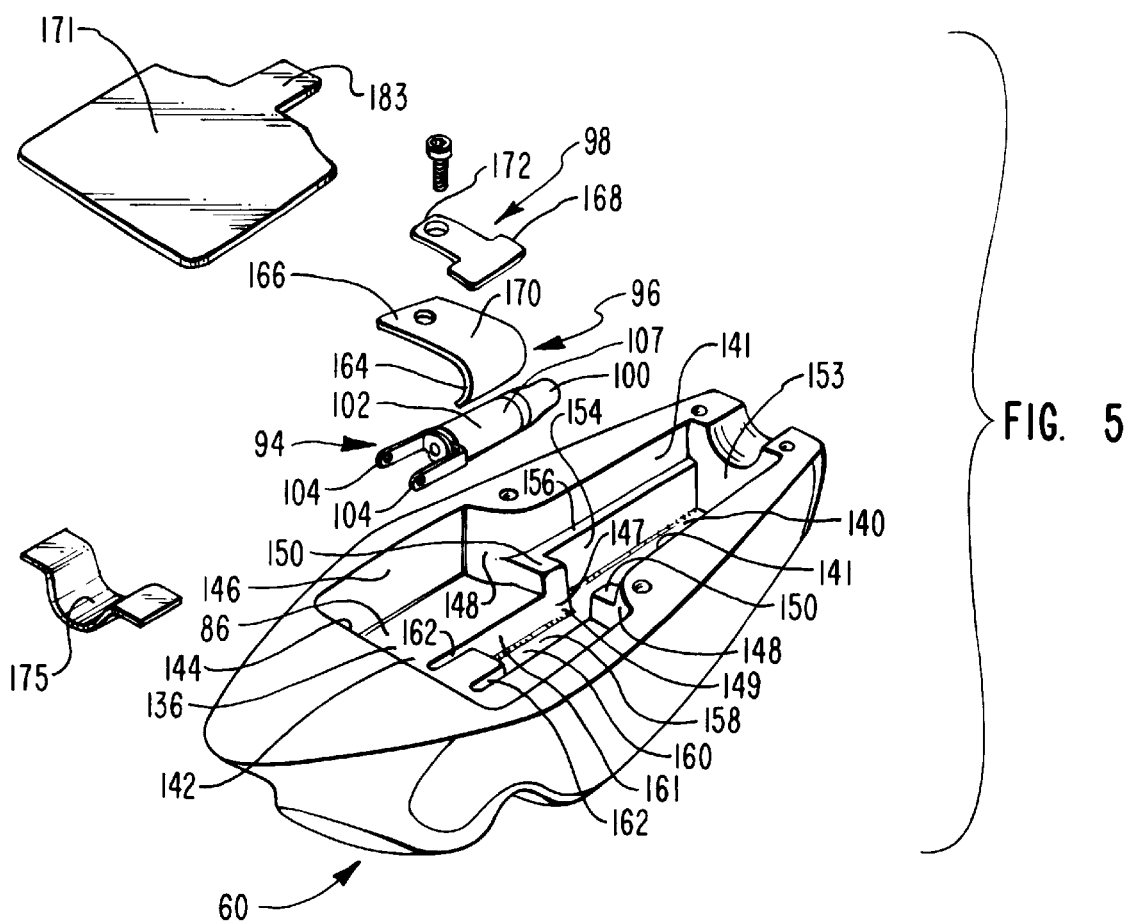
FIG. 5 is a view of the interior surface of the bottom lid and an exploded view of the lamp assembly, harness, clamp, and further including a lid and strap employed in an alternate embodiment of the portable endoscopic camera of FIG. 1.

In one presently preferred embodiment of a light source means, as shown in FIGS. 3–5, an incandescent lamp assembly 94 comprises a bulb 100 having a focused end lens and a base preferably disposed within a socket 102, socket 102 having feet 104. In one embodiment, a proximal portion of lamp assembly 94 comprises feet 104.

Preferably, the invention further comprises means for focusing the light produced by the light source into the lens means. As an example, a distal portion of lamp assembly 94, such as bulb 100, is preferably disposed through input port face 114 of collar 113, such that bulb 100 is disposed directly against fiber bundle 112, providing a more efficient design by focusing more light directly into fiber bundle 112. In one embodiment, the distal portion of lamp assembly 94 comprises bulb 100.

In another embodiment, the distal portion of lamp assembly 94 comprises bulb 100 and a portion of socket 102 distal from feet 104. By disposing socket 102 within collar 113 along with bulb 100, additional light is focused into fiber bundle 112. In yet another embodiment, however, it is convenient to refer to an intermediate portion as a portion of lamp assembly 94 proximal to the portion of lamp assembly 94 disposed through input port face 114, yet distal to feet 104. For example, in one embodiment, wherein only bulb 100 is disposed through input port face 114, the portion of socket 102 distal to feet 104, yet proximal to bulb 100, is an intermediate portion.

In another embodiment, the means for focusing the light produced by the light source means into the lens means comprises the outer diameter of bulb 100 being approximately the same as the outer diameter of fiber bundle 112. A bulb having a greater diameter is less efficient, focusing less light into fiber bundle 112. The discussion below relating to the housing means will provide additional examples of means for focusing the light produced by the light source means into the lens means as well as examples of means for retaining the light source means in an abutting relationship with the lens means.

By way of example, one presently preferred light source means is a 222 miniature incandescent bulb having a focused end lens and a recommended voltage of approximately 2.4 volts.

D. The Video Camera

As indicated above, the lens means is optically coupled to the video imaging means for translating an image of the illuminated object from the distal end of the lens means to the video imaging means. The video imaging means is comprised of a (i) sensor array coupled to the lens means and (ii) conversion means, electrically coupled to the sensor array, for converting images translated by the lens means and impinging upon said sensor array into video signals, and for outputting the converted video signals.

Figure 2:
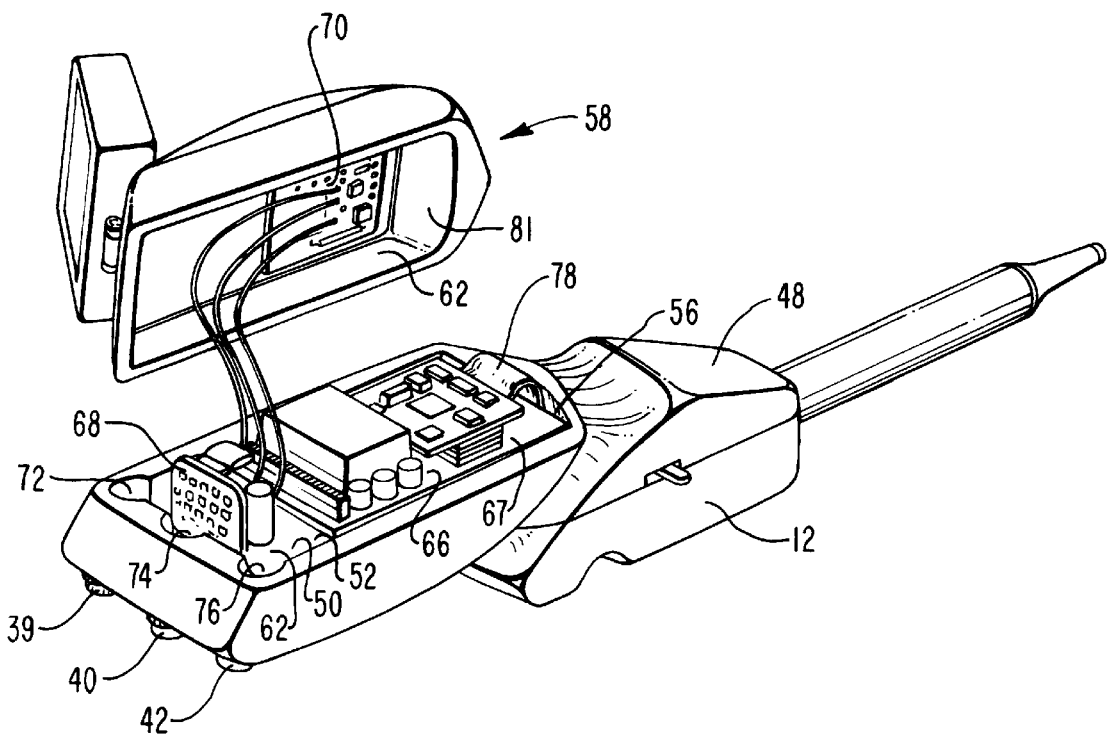
FIG. 2 is a perspective view of the portable endoscopic camera of FIG. 1 with the top of the camera housing removed.

By way of example, one presently preferred embodiment of a video imaging means is a camera assembly 67 as shown in FIGS. 2–4. Camera assembly 67 has a plurality of vertically stacked printed circuit boards 66 attached by a ribbon cable 78 to a CCD array circuit board 80. By vertically stacking the printed circuit boards 66, camera assembly 67 is able to fit more readily in a hand-held housing means. CCD printed circuit board 80 of camera assembly 67 includes a CCD sensor array 91 coupled to the proximal end of the lens means.

An example of a preferred video imaging means is a camera assembly 67 comprised of a KST-90 CCD camera assembly, available from KOWA Optimed, Inc. Torrance, Calif.

E. The Optical Coupler

The invention further comprises a means for optically coupling the lens means to the video imaging means. For example, as shown in FIGS. 3–4, camera coupler 90 is provided to couple an image under examination from lens tube 32 into CCD array 91 on CCD array printed circuit board 80. Coupler 90 includes a housing having a distal end 116 and a proximal end 118. The housing of coupler 90 further has an interior surface 120 defining a tubular passageway 121 and an exterior surface 122 defining a cylinder at distal end 116 and a square-shape at proximal end 118.

Square-shaped proximal end 118 of exterior surface 122 of coupler 90 includes opposing parallel side walls 124, each of which are perpendicular to a bottom wall 126. Attachment members 129 affix proximal end 118 of coupler 90 to CCD array circuit board 90, through the use of screws for example. The proximal end (not shown) of tubular passageway 121 surrounds CCD array 91 while the distal end 123 of tubular passageway 121 slidably surrounds proximal portion 108 of lens tube 32. Coupler 90 thus completely encloses CCD array 91 and proximal end 108, preventing stray light from corrupting the image received by CCD array 91 from lens tube 32.

With continued reference to FIGS. 3–4, as an additional aspect, the invention further includes focusing means, coupled to the sensor array, for focusing the translated image of the object onto the sensor array by adjusting the distance separating the sensor array and the proximal end of the lens means. In one embodiment, the focusing means is configured to receive the means for optically coupling the lens tube to the video imaging means. An example of this embodiment of a focusing means includes focusing bridge 92.

Focus bridge 92 features a U-shaped member including a beam 130, beam 130 having a horizontal axis. A pair of support members 132 extend vertically upward with respect to the horizontal axis of beam 130 from opposing ends of beam 130. Beam 130 and support members 132 define a U-shaped channel 133. Each support member 132 includes a flange 28 extending outwardly with respect to the U-shaped channel from the respective support member 132, each flange 28 parallel to the horizontal axis of beam 130. U-shaped channel 133 of focus bridge 92 is thus configured to receive square-shaped proximal end 118 of exterior surface 122 of camera coupler 90.

Distal face 127 of beam 130 is preferably notched to allow it to mate with proximal cylindrical face 134 of camera coupler 90. In the preferred embodiment, support members 132 of focus bridge 92 are disposed distal to attachment members 129 of camera coupler 90. Thus, camera coupler 90 fits within U-shaped channel 133 of focus bridge 92 such that support members 132 are disposed snugly between attachment members 129 and face 134.

It will be appreciated that in one embodiment, beam 130 of focus bridge 92 is disposed against bottom wall 126, focus bridge 92 cradling camera coupler 90, as shown in FIG. 3. Focus bridge 92 thus assists in preventing movement laterally and in a vertical plane and in maintaining camera coupler 90 along the longitudinal axis of lens tube 32. It will also be appreciated from the foregoing description that, in an alternative embodiment, beam 130 of focus bridge is disposed against top wall 128, side walls 124 being perpendicular to top wall 128.

As focus bridge 92 is positioned back and forth, interior surface 120 of distal end 116 of camera coupler 90 slides back and forth on proximal portion 108 of lens tube 32. As discussed previously, CCD array circuit board 90 is affixed to proximal end 118 of camera coupler 90, while distal end 116 of tubular interior surface 120 of camera coupler 90 slidably surrounds proximal portion 108 of lens tube 32. Thus, selective positioning of focus bridge 92 selectively positions CCD array 91 with respect to lens tube 32.

F. The Power Supply

The power supply means will now be discussed with reference to FIG. 1. The video imaging means, light source means, transmitter means, and display means are electrically coupled to and receive electrical power from the power supply means. By way of example, with reference to FIG. 1, a rechargeable battery pack 35, possibly including a Nicad cell, is disposed on the housing means to act as a power supply means. Battery pack 35 is similar to the battery pack of a cellular phone, for example. Disposable batteries or a rechargeable acid lead cell are additional examples of power supply means. The invention also includes a means for regulating the voltage produced by the power supply means, such as a voltage regulator printed circuit board 68.

If cordless, battery operated power is not desirable, the operator may selectively employ power outlet supply port 39 for connecting to cord-operated power as power supply means. It will be appreciated that the term "cordless" as used throughout this specification and claims refers to a camera which does not have an external cord, cable or wire extending externally from the camera housing for attachment to a power supply means, light source means, display means or other mechanism which is not contained within or disposed on the housing. An example of camera 10 in the cordless mode is currently demonstrated in FIG. 1. It will also be appreciated that "cord-operated" refers to a camera which employs at least one cord, cable or wire for attachment to a power supply means, light source means, display means or other mechanism which is not contained within or disposed upon the housing. It will also be appreciated that camera is selectively operable in cordless mode and a cord-operated mode.

As one example of a cord-operated power supply, if battery use is not desired, it is possible to power camera 10 with power from an electrical outlet by using a transformer, such as a 12 volt output wall plug transformer.

G. The Video Display

Various examples of display means will now be discussed. In one embodiment, the video signal produced within the video imaging means is output through the conversion means to an integral display means mounted on or within the housing means, the display means electrically coupled to the video imaging means for displaying video images of the object. One example of a such a display means is monitor 36, shown in FIG. 1 mounted by hinge 38 on a housing means. Monitor 36 is preferably demountably mounted on the housing means such as with a dual pronged plug similar to a wall outlet plug. In another embodiment, a monitor is disposed integrally within a proximal end of the housing means such that it can be viewed by viewing the proximal end. Monitor 36 is preferably a liquid crystal display monitor, such as Citizen LCD monitor, M329-1A, available from CBM Corporation, Japan or a similar, smaller unit. Additional examples of display means include a video monitor, a printer, and a variety of other display means within the art.

In another embodiment, the video signal produced within the video imaging means is output through the conversion means to a separate display means, such as a wall mounted monitor, or a monitor disposed on a desk or a stand. As shown in FIGS. 1–2, the provision of S-VHS output port 40 and composite output port 42 allows portable endoscopic camera 10 to be selectively connected to one or more of such external monitors. Ports 40, 42 are electrically coupled to the video imaging means. S-VHS port 40 allows portable endoscopic camera 10 to output video signals to monitors in a variety of countries. In another embodiment the video signal produced within the video imaging means is output through the conversion means to a monitor mounted on or within the housing means and to a separate monitor.

H. The RF Transmitter/Receiver

In another embodiment, the video signal produced within the video imaging means is output through the conversion means to a transmitter means, electrically coupled to the video imaging means, for transmitting video signals generated by the video imaging means. A receiver means is designed for receiving the video signals transmitted by the transmitter means. A display means, examples of which have been previously discussed, is electrically coupled to the receiver means for displaying video images of the object.

One example of a transmitter means is signal unit 70, shown in FIG. 2. In one presently preferred embodiment, signal unit 70 is a video transmitter WVT-1, available from Pragmatic Communication Systems, Inc., Sunnyvale, Calif. Also by way of example, in one embodiment, the receiver means comprises video receiver RCV915, of Pragmatic Communication Systems, Inc.

The use of the transmitter means, receiver means, and electrically coupled display means allows the operator to transmit video images from a remote location to a central monitor, for example. Thus, a clinic having a variety of rooms is not required to wire each of the rooms for endoscopic capability.

In another embodiment, the video signal produced within the video imaging means is output through the conversion means to a means for recording the video images of the inspected object. For example, the installation of a memory chip within the housing means or within a supplemental casing means, for example, allows the practitioner to digitally record video images within the chip, then download the recorded information at a later time.

I. The Housing

As another aspect of the invention, the housing means will now be discussed in detail. In order to house the components of the invention, a variety of housing means are available, such as housing 12, shown in FIG. 1. It will be appreciated that housing 12 of FIG. 1 is an example of a hand-held means for housing the light source means, video imaging means, lens means, and power supply means, such that the apparatus is self-contained and convenient to manipulate. In the embodiment of FIG. 1, the light source means is internal within the housing 12, rather than external to the housing 12, as in a typical cord-operated system.

As shown in FIG. 1, housing 12 has an exterior surface 14, a distal end 16, a proximal end 18, a top surface 20, a bottom surface 22, and opposing sides 24. Monitor 36 is hingeably mounted on proximal end 18 of housing 12. Battery pack 35 is disposed on top surface 20 of housing 12. In the embodiment of FIG. 1, a probe adaptor 30 projects from distal end 16 and couples lens tube 32 of module 88 to a probe 34.

Housing 12 further includes gripping grooves 44 and 46, which aid the user in securely grasping camera 10. Gripping groove 44 is configured to approximate the contour of an adult hand between the thumb and forefinger, and gripping slot 46 is configured for partial insertion of the third, fourth, and/or fifth fingers during use. Housing 12 is balanced such that the practitioner can grip gripping groove 44 with the thumb and forefinger and rest a proximal portion of the bottom surface 22 on the practitioner's hand or wrist. By gripping gripping groove 44 or other areas of the contoured housing, the practitioner is able to successfully control the direction and orientation of the endoscopic camera. Slip proof tape is also preferably disposed on the surfaces where gripping is expected.

With reference now to FIGS. 2 and 3, housing 12 is comprised of a housing body 48 having an interior surface 50. Interior surface 50 defines a top cavity 52, a bottom cavity 54, and an internal passageway 56 linking top cavity 52 and bottom cavity 54. A segmented hollow top lid 58 covers top cavity 52 while a segmented hollow bottom lid 60 covers bottom cavity 54. Top cavity 52 and the interior surface 81 of corresponding top lid 58 define a top chamber 62, while bottom cavity 54 and the interior surface 86 of corresponding bottom lid 60 define a bottom chamber 64.

The segmentation of housing 12 allows for an efficient use of space and weight distribution, which increases the practitioner's ability to hold and operate light-weight, hand-held portable endoscopic camera 10.

In a preferred embodiment, housing 12 defames a collar 119 disposed about distal hub 115 for retaining lens fiber module 88 in a fixed position with respect to housing 12. A portion of collar 119 is defined by a recess 151 within distal end 152 of bottom lid 60 while a corresponding portion of collar 119 is defamed by a recess (not shown) within the distal end 49 of housing body 48. By disposing distal hub 115 in collar 119 and proximal hub 117 proximal to collar 119, lens-fiber module 88 is engaged in an interlocking relationship with housing 12, as shown in FIG. 3. Adding adaptor 30 to lens tube 32 enhances the interlocking relationship.

With reference now to FIG. 2, top chamber 62 houses the plurality of vertically stacked printed circuit boards 66, preferably three printed circuit boards of camera assembly 67. The disposition of the vertically oriented boards 66 within top chamber 62 allows camera assembly 67 to be inserted into a thin housing. Ribbon cable 78 of camera assembly 66 extends into internal passageway 56 and attaches to CCD array printed circuit board 80 of camera assembly 67 within bottom chamber 64 (shown in FIG. 3).

With continued reference to FIG. 2, top chamber 62 also houses voltage regulator circuit board 68, signal unit 70, power supply port 39, S-VHS outlet port 40, and composite outlet port 42. Top cavity 52 includes a first proximal recess 72, a second proximal recess 74, and a third proximal recess 76 for disposition of power supply port 39, S-VHS outlet port 40, and composite outlet port 42 and their associated wiring therein, respectively. The interior surface of top lid 58 is contoured to cover the vertically stacked circuit boards 66 of camera assembly 67 and is contoured to receive signal unit 70.

As shown in FIGS. 1–3, housing 12 further includes a pair of opposing focus adjustment slots 26 disposed within sides 24. Opposing focus adjustment flanges 28 of focus bridge 92 project from opposing adjustment slots 26 for adjusting the focus of portable endoscopic camera 10. Each slot 26 is configured in a rectangular shape to allow each flange 28 to slide in a front to rear and rear to front direction. As will be discussed in additional detail below, in one embodiment, beam 130 of focus bridge 92 is suspended within adjustment notch 136 of bottom lid 60. Opposing adjustment flanges 28 are slidably suspended on the opposing edges 138 of bottom lid 60 within opposing adjustment slots 26 of housing body 48.

Focus bridge 92 thus serves as an example of means for focusing the translated image of the object onto the sensor array by adjusting the distance separating the sensor array and the proximal end of the lens means and for maintaining the longitudinal axis of the lens means. The performance of both of these functions is a significant contribution to the art.

The lens means and the light source means are closely aligned within bottom chamber 64, which is specifically designed to fit only certain components and is separate from a variety of the other components of portable endoscopic camera 10. Housing all of the components of portable endoscopic camera 10 within the same chamber would require a large chamber, allowing increased dissipation of light. As a result of applicant's chambering, light from the light source means is essentially retained within a single, relatively smaller chamber, and is focused into the lens means. Therefore, dual chambered housing 12 is an example of a focusing means for focusing the light produced by the light source means into the lens means.

Interior surface 86 of bottom lid 60 will now be described in detail with reference to FIG. 5. It will be appreciated that two major goals of bottom chamber 64 are (1) to prevent the movement of the components associated closely with the light source; yet (2) permit the back and forth sliding movement of sensor array circuit board 80. In order to accomplish each of these objectives, interior surface 86 of bottom lid 60 includes a bottom lid floor 158, wide adjustment notch 136, a thinner, deeper, input port reception channel 140, bottom lid upper distal walls 141, and a lamp assembly reception channel 160.

Adjustment notch 136 is defined by an adjustment notch floor 142, a proximal wall 144, opposing side walls 146, opposing proximal ends 148 of opposing bottom lid upper distal walls 141, and the imaginary plane extending between and upwardly from the proximal faces of posts 150. However, in the preferred embodiment, sensor array circuit board 80 is only allowed to move back and forth within a proximal portion of the adjustment notch 136.

Channel 160 is an example of a means for retaining the light source means in an abutting relationship with the lens means. Channel 160 is formed in the floor 142 of adjustment notch 136 and is configured at a distal portion to receive collar 113 of fiber light input port 110. Channel 160 is bordered at a distal end by an imaginary plane extending between the distal faces of opposing posts 150. Socket feet notches 162 of channel 160 each receive a corresponding socket foot 104, each notch 162 having a surface below the floor of adjustment notch 136, yet above the surface of channel 160.

Input port reception channel 140 is designed for reception of fiber light input port 110 of fiber-lens module 88. Channel 140 is defined by the distal end 153 of interior surface 86 of bottom lid 60, opposing input port channel side walls 154, opposing posts 150, a distal portion of lamp assembly reception channel 160 and the lower portion of the bottom lid upper distal walls 141. Ridges 156 are located slightly lower than the upper edges 155 of input port 110 as input port 110 is received in channel 140. A distal portion of channel 140 may be slightly wider than the upper edges 155, such that the upper edges 155 do not rest upon ridges 156. Alternatively, channel 140 is configured such that upper edges 155 are disposed upon ridges 156. Channel 140 is therefore another example of means for retaining the light source means in an abutting relationship with the lens means.

Opposing posts 150 extend upwardly from bottom lid floor 158. Opposing proximal side walls 161 of channel 160 extend proximally with respect to a bottom portion 147 of opposing posts 150, the inner face 149 of each bottom portion 147 serving as a distal wall of channel 160.

Fiber light input port 110 is disposed within input port reception channel 140 such that a distal portion of lamp assembly 94 is disposed through face 114 of fiber light input port 110. Thus, bulb 100 abuts fiber bundle 112 and collar 113 is disposed about the distal portion of lamp assembly 94. The disposition of a distal portion of lamp assembly 94 through input port face 114 creates a light focusing chamber within cylindrical collar 113 for focusing light produced by the light source means into the lens means. Thus, cylindrical collar 113 serves as another example of a means for focusing the light produced by the light source means in the lens means.

In one embodiment, edge 111 of collar 113 is maintained between bottom portion 147 of posts 150. In another embodiment, edge 111, or alternatively, the entire collar 113 is disposed proximally such that it is maintained between opposing side walls 161. In both embodiments, collar 113 of input port 110 extends into channel 160.

Lamp assembly reception channel 160 and input port reception channel 140 thus combine to form a single illumination channel, which acts as a means for focusing the light produced by the light source means into the lens means and as a means for retaining the light source means in an abutting relationship with the lens means.

As an additional example of a means for retaining the light source means in an abutting relationship with the lens means, a harness 96 is disposed about lamp assembly 94 and, in one embodiment, is secured to floor 142 of adjustment notch 136. A curved end 164 of harness 96 is disposed about socket 102 of lamp assembly 94, maintaining lamp assembly 94 tightly within harness 96 such that lamp assembly 94 is suspended within channel 160. In one embodiment, flat end 166 of harness 96 is secured to floor 142 of adjustment notch. By suspending lamp assembly 94 away from the walls and floor of channel 160 within harness 96, heat is allowed to dissipate within channel 160.

Another example of a means for retaining the light source means in an abutting relationship with the lens means is a T-shaped harness clamp 98, which is preferably disposed over harness 96 and secured to adjustment notch floor 142 as shown in FIG. 4, adding additional leverage to maintain lamp assembly 94 in a fixed position. Returning to FIG. 5, top portion 168 of T-shaped harness clamp 98 abuts outer surface 170 of harness 96 in mating relationship. The bottom portion 172 of T-shaped clamp 98 is secured to floor 142.

Figure 6:
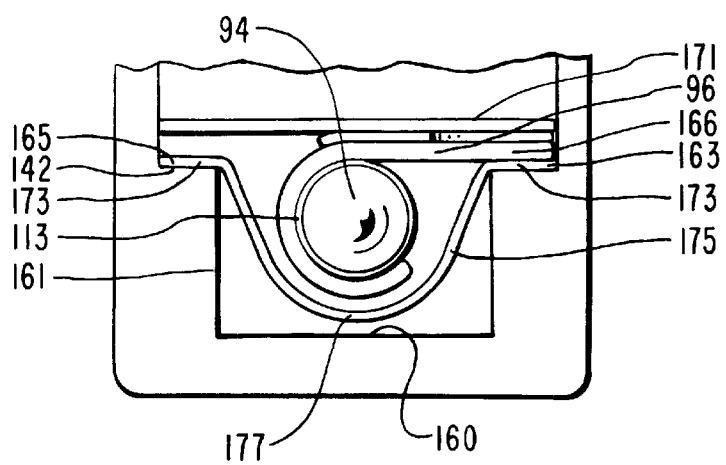
FIG. 6 is a cross-sectional view of the assembled components of FIG. 5.

As another example of a means for focusing light produced by the light source means into the lens means, a flat lamp assembly lid 171 as shown in FIGS. 5 and 6 is disposed over the lamp assembly 94, forming a light focusing chamber. FIG. 6 is a cross-sectional view in the proximal direction of an assembled FIG. 5 taken proximal to posts 150. With Lid 171 and strap 175, light is further focused along the longitudinal axis of lamp assembly 94 into fiber bundle 112 rather than perpendicular to the longitudinal axis and away from fiber bundle 112. By way of example, lid 171 may cover lamp assembly reception channel 160, the entire floor 142 of adjustment notch 136 or both. Optionally, lid 171 is configured with a narrow neck 183, for example, which extends between posts 150. Preferably the lid is snapped in place.

In another embodiment, as shown in FIGS. 5 and 6, the means for focusing light produced by the light source means into the lens means comprises lid 171 and a strap 175. By way of example, in one embodiment strap 175 is rectangular in shape. In another embodiment, strap 175 is square in shape. Strap 175 is made from a variety of materials such as ABS plastic and is disposed between proximal opposing side walls 161 and under at least portions of both lamp assembly 94 and collar 113.

A first upper end 163 of strap 175 is preferably attached under flat end 166 of harness 96 on adjustment notch floor 142. A second upper end 165 of strap 175 is disposed on an opposing side of floor 142 such that the distal face of opposing upper portions of strap 175 are adjacent or abut the proximal faces of posts 150. An intermediate portion 177 of strap 175 extends between ends 163 and 165.

As discussed previously, a distal portion, such as bulb 100, of lamp assembly 94 is surrounded by collar 113. Collar 113, or at least a proximal portion thereof, such as edge 111, is maintained between opposing proximal side walls 161 in channel 160 such that a distal portion of strap 175 is disposed under collar 113, or at least a proximal portion thereof. Strap 175 then also extends proximally under a portion of lamp assembly 94, such as an intermediate portion of lamp assembly 94 (e.g., the portion of socket 102 distal from feet 104). Lid 171 is disposed above lamp assembly 94 and collar 113 as shown in FIG. 6, such that light is focused by strap 175 and lid 171 into the lens means.

While in one embodiment, strap 175 abuts collar 113 and lamp assembly 94, in another embodiment, as shown in FIG. 6, strap 175 is disposed slightly below collar 113 and lamp assembly 94, allowing collar 113 to be disposed about the distal portion of lamp assembly 94 during manufacture.

As another example of a means for focusing light produced by the light source means into the lens means, a cylindrical light focusing chamber, such as a sleeve (not shown) having a diameter approximately the same size as the diameter of collar 113 surrounds an intermediate portion of lamp assembly 94. The sleeve abuts the proximal edge 111 of collar 113. Optionally, the chamber is a cylindrical metal housing.

By isolating the optics together with the light source in one chamber and the signal unit and the majority of the camera components in another chamber, damage to one chamber may be isolated to that chamber. Furthermore, a desired adjustment of lenses or light bulbs does not require an opening of the entire device. Any required maintenance is likely to occur within bottom chamber 64, allowing the components of top chamber 62 to remain uniquely housed in a relatively maintenance free environment, preventing damage to the top chamber components during maintenance.

The configuration also employs space more efficiently. While the majority of top chamber 62 is oriented proximal to bottom chamber 64, a significant portion of the top chamber 62 is oriented above a significant portion of bottom chamber 64, allowing a portion of the contents of top chamber 62 to be stacked above a portion of the contents of bottom chamber 64, or in an alternative embodiment, at least allowing ribbon cable 78 to be disposed within internal passageway 56. This configuration of housing 12 provides for a balanced orientation in the practitioner's hand. This use of space in a balanced, completely hand-held, portable endoscopic camera is a significant advance within the field.

Also in the preferred embodiment, housing 12 includes a means for replacing the light source means. For example, in one embodiment, the means for replacing the light source means comprises a door (not shown) on bottom lid 60 for the replacement of the incandescent lamp. The door may, for example, comprise a sliding door as typically seen in a variety of remote control devices for the replacement of batteries. In another embodiment, the means for replacing the contents of the bottom chamber comprises bottom lid 60 configured to snap off the housing body. In another embodiment, the bottom lid is spring loaded on the housing body.

Disposing lamp assemble 94 near proximal end 18 of housing 12 within top cavity 52 behind voltage regulator circuit board 68, or near a corner recess such as 72, or 76, for example, may assist in providing access to lamp assembly 94 for maintenance thereof. A door, such as described above could be conveniently located near the lamp assembly 94. This would require a extension of input port 110 or another means for coupling lamp assembly 94 to input port 110, such as a cable or a fiber bundle extending from input port 110 to lamp assembly 94.

Figure 7:
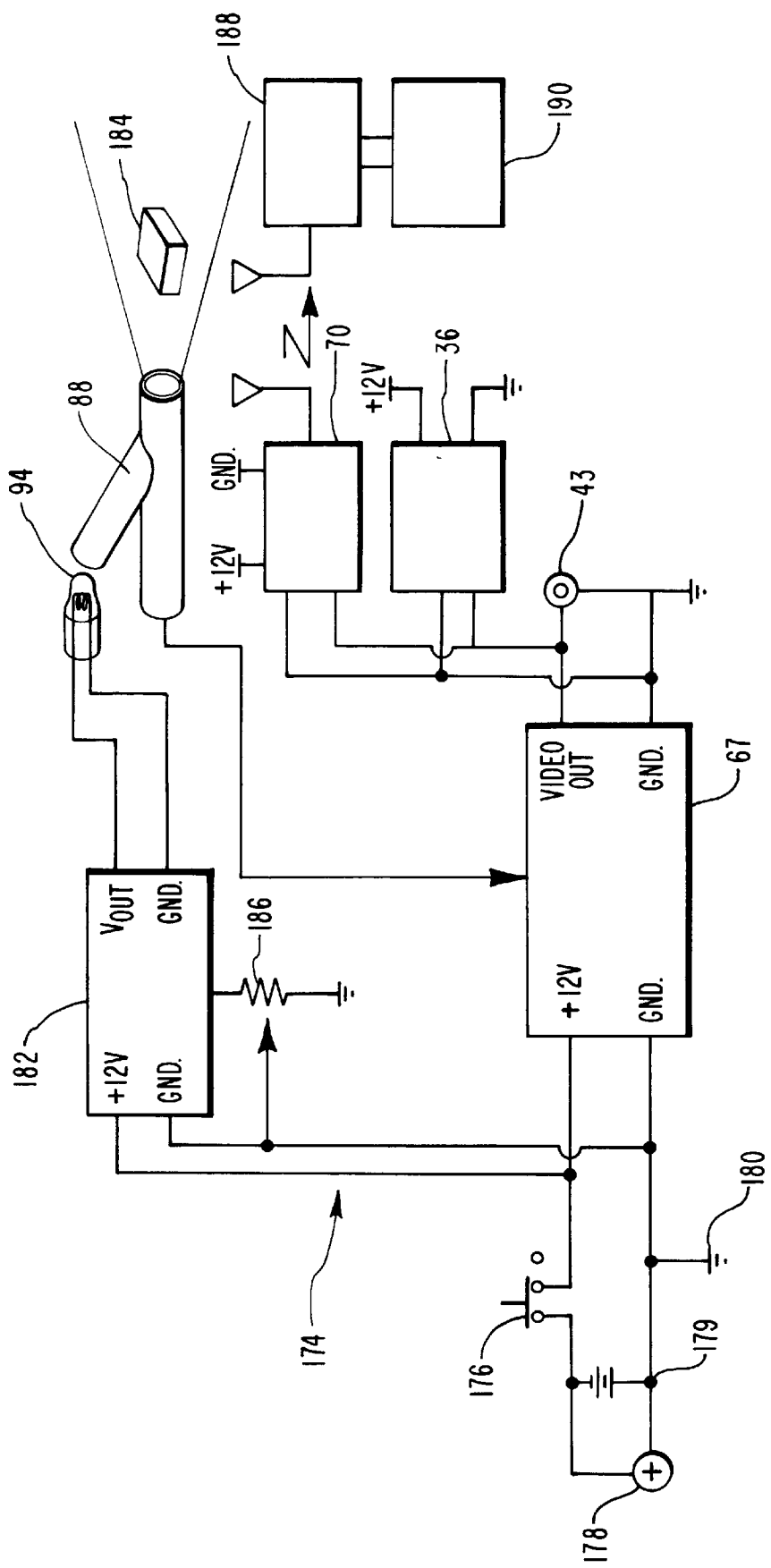
FIG. 7 is a wiring diagram of the portable endoscopic camera of FIG. 1.

With reference now to FIG. 7, the wiring diagram 174 of one presently preferred embodiment of camera 10 is disclosed. Wiring diagram 174 discloses an on/off switch 176 electrically coupled to an outlet power source 178 which is electrically coupled to ground 180. Battery power source 179 is also disclosed. A power supply of 12 volts is employed in the presently preferred embodiment.

Power is also directed to a voltage regulator 182 for converting the power to approximately 2.5 volts to approximately 3.5 volts. The higher voltage of 3.5 volts generates greater intensity in lamp assembly 94 and is presently preferred, but also wears the bulb faster. It is possible to adjust the light intensity through the use of a potentiometer 186, which serves as an example of intensity adjustment means, electrically coupled to the light source means, for varying the intensity of the light produced by the light source means. Potentiometer 186 is actuated, for example through the use of a set screw disposed in housing 12.

Lamp assembly 94 receives the reduced voltage charge and illuminates lens-fiber module 88, which, in turn illuminates an object 184 under examination. An image of object 184 is received within lens tube 32 and directed into camera assembly 67. Camera assembly 67 directs the image into a cord operated output port 43, such as a composite video output port and/or an S-VHS video output port, and to monitor 36, and signal unit 70. Receiver 188 receives the video signals transmitted by signal unit 70 and is coupled to display 190, such as a wall mounted display for displaying video images of object 184. A switch may be required to alternate between composite output and S-VHS output.

As shown in FIG. 3, power wires 192 connecting lamp assembly 94 to voltage 68 extend through internal passageway 56 of housing body. It will be appreciated that a variety of wiring possibilities are available to accomplish the intent of wiring diagram 174 and that one skilled in the art will understand how to wire the various components of portable endoscopic camera 10 based on disclosures made herein.

J. Alternative Housing Embodiment

Figure 8:
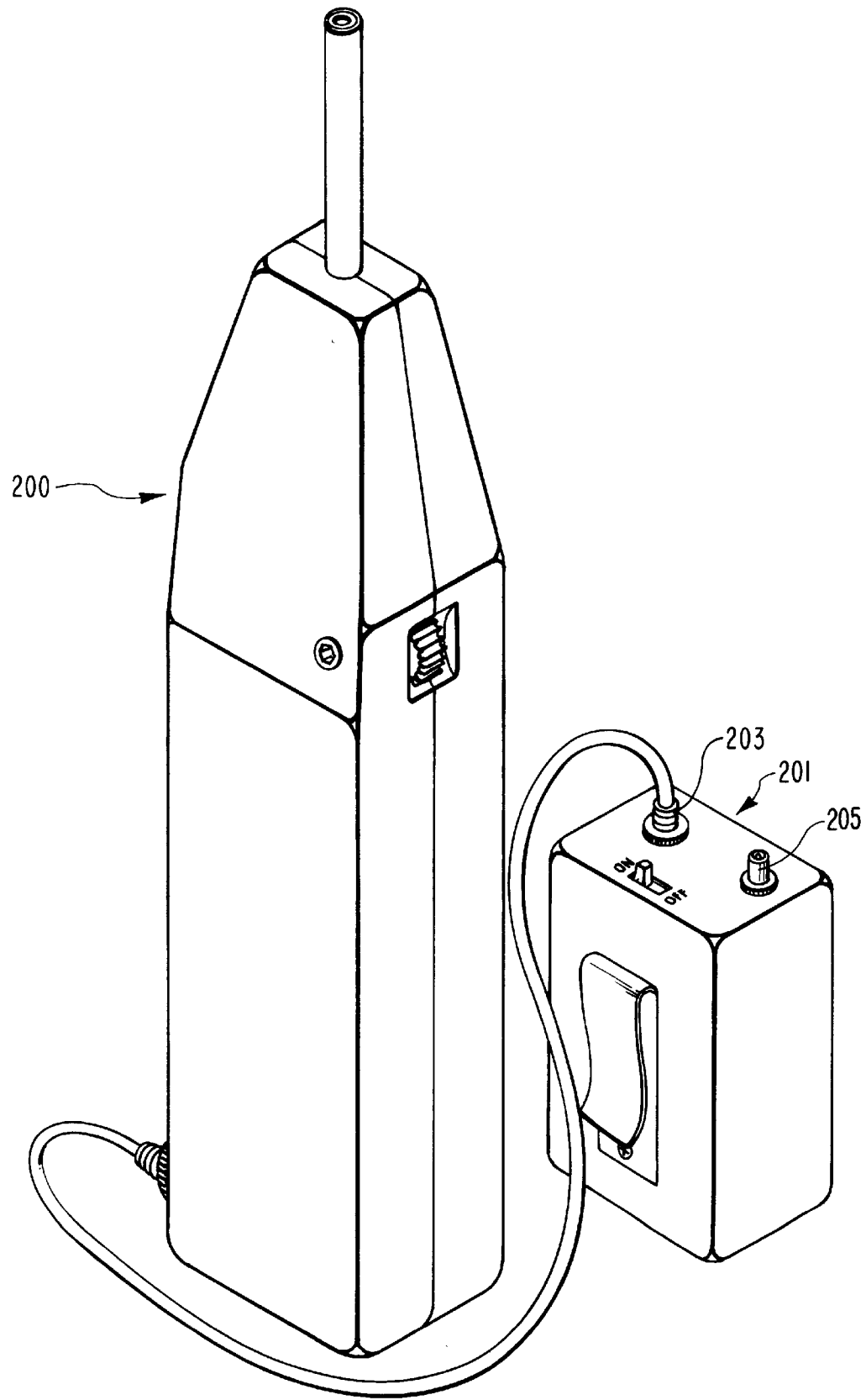
FIG. 8 is a perspective view of another embodiment of a portable endoscopic camera.
Figure 9:
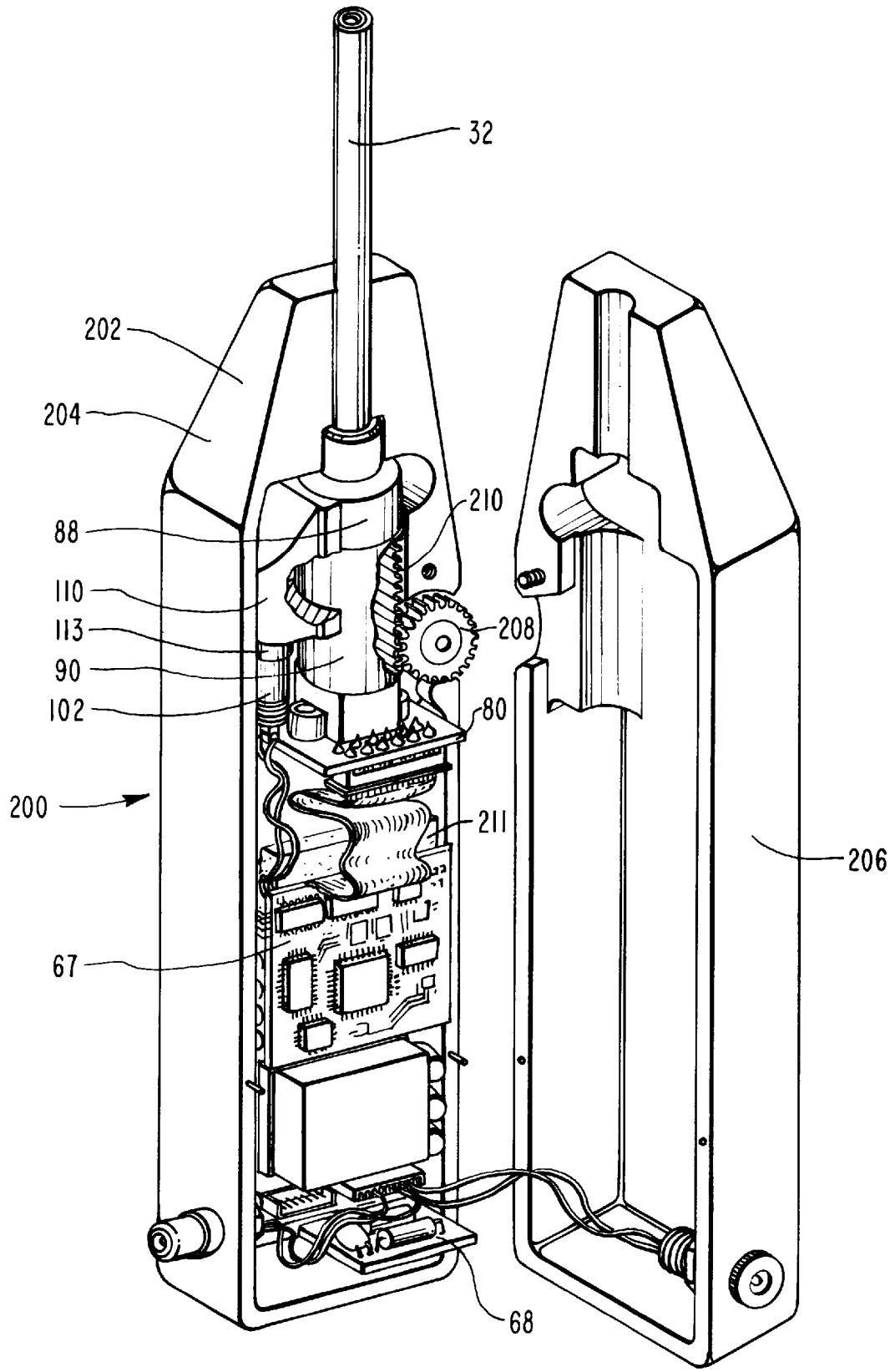
FIG. 9 is a view of the portable endoscopic camera of FIG. 8 with the lid of the housing removed.

Another example of a portable hand-held endoscopic camera 200 is shown in FIG. 8. As shown in FIG. 9 and as discussed previously with reference to endoscopic camera 10, portable endoscopic camera 200 includes voltage regulator circuit board 68 electrically coupled to camera assembly 67, which is coupled through coupler 90 to lens fiber module 88. Also as discussed previously with regard to portable endoscopic camera 10, bulb 100 of lamp assembly 94 directly abuts fiber bundle 112 of fiber light input port 110. Socket 102 may be surrounded by a clip or harness maintaining bulb 100 within fiber light input port 110, or the housing 202 may be configured to retain bulb 100 within fiber light input port 110. Optionally, lamp assembly 94 may be retained within a cylindrical light focusing chamber, such as a sleeve, (such as discussed previously, for example) abutting proximal edge 111 of collar 113. In one embodiment, the wiring of endoscopic camera 200 is as previously disclosed in the wiring diagram of FIG. 7.

While focus bridge 92 may be employed in this embodiment with minor adjustments, thumb wheel 208 serves as another example of means for focusing the translated image of the object onto the sensor array by adjusting the distance separating the sensor array and the proximal end of the lens means and for maintaining the longitudinal axis of the lens means. Thumb wheel 208 engages interlocking ridges 210 disposed on the exterior surface of camera coupler 90, sliding camera coupler 90 along proximal portion 108 of lens tube 32, thus allowing one to position the CCD array, thereby focusing the camera. Thumb wheel 208 also assists in preventing lens-fiber module 88 from moving in a lateral direction toward the sides of housing 202, thus maintaining the longitudinal axis of the lens means. Mechanical stop 211 is provided proximal to CCD array circuit board 80 to prevent camera coupler 90 from sliding off the proximal portion 108 of lens tube 32.

It will be appreciated that portable endoscopic camera 200 may be adapted with a variety of features discussed previously with regard to portable endoscopic camera 10. For example, a variety of light source means, as discussed previously are also available for use in camera 200, including external bulbs, bulbs within an external enclosure, and bulbs coupled through a cable, such as a fiber optic cable, to the lens means. Also by way of example, in one embodiment, a power supply means such as battery pack 35 demonstrated in FIG. 1, is mounted on housing 202. In another embodiment, disposable batteries or a rechargeable acid lead cell are disposed within housing 202. A variety of other power supply means are also available, including cord-operated power.

Similarly, various display means are electrically coupled to the camera assembly 67 within housing 202. For example, in one embodiment, the display means is a monitor, such as monitor 36 of FIG. 1, mounted on housing 202. Cord-operated composite video output capability, S-VHS output capability, may also be provided within housing 202, as well as transmitter means.

Thus, housing 202 is another example of hand-held means for housing the light source means, video imaging means, lens means, and power supply means, such that the apparatus is self-contained and convenient to manipulate. As shown in FIG. 9, single chambered housing 202 includes a housing body 204 and a corresponding lid 206, the interior surfaces of housing body 204 and lid 206 defining a single chamber.

In yet another embodiment, camera 200 is electrically coupled to the contents a supplemental casing means such as case 201, shown in FIG. 8. Case 201 is conveniently held in a practitioner's hand or mounted on the practitioner's belt, for example. It will also be appreciated that in yet another embodiment, camera 10 of FIG. 1 is electrically coupled to the contents of case 201. Case 201 includes an outlet port 203 for electrically coupling to the contents of case 201. In one embodiment, case 201 contains a power supply means electrically coupled to, and for supplying electrical power to the light source means, video imaging means, transmitter means, and/or display means. Case 201 may also conveniently house a transmitter means, or light source means (such as a halogen bulb in the range of 50 to 100 watts, for example) connected through a cable to the lens means. Outlet port 205 is employed for connection to optional cord-operated power supply means, or separate display means such as a wall or desk mounted monitor.

Figure 10:
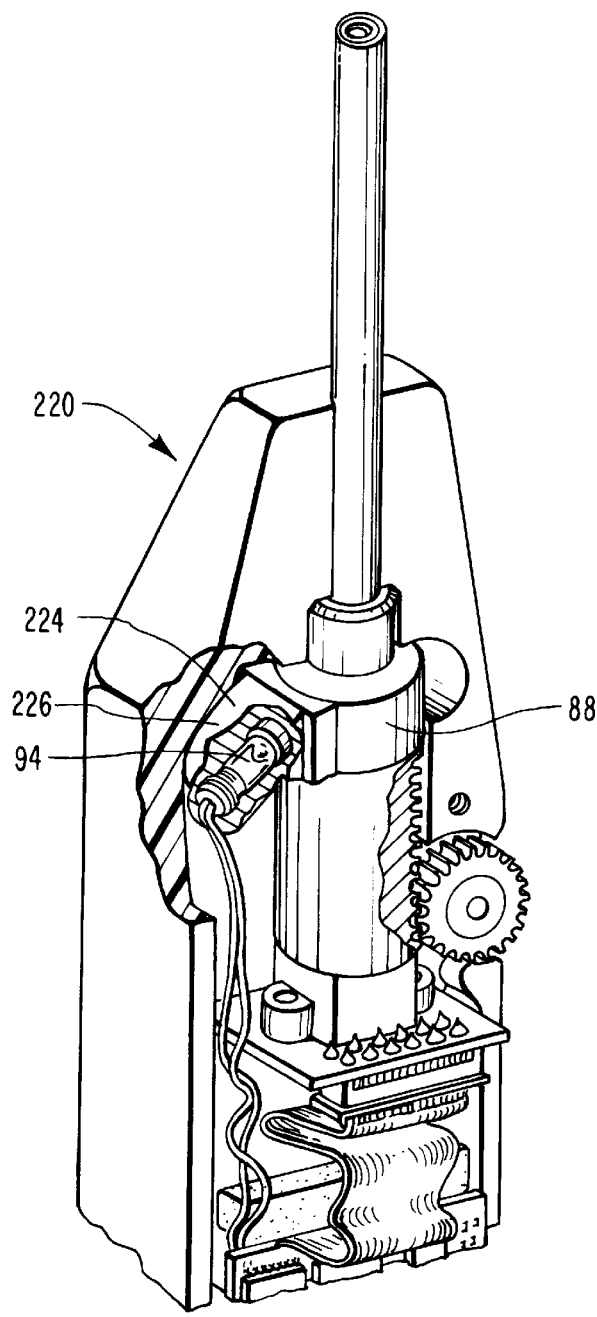
FIG. 10 is a partial view of yet another embodiment of a portable endoscopic camera with the lid of the housing removed.
Figure 11:
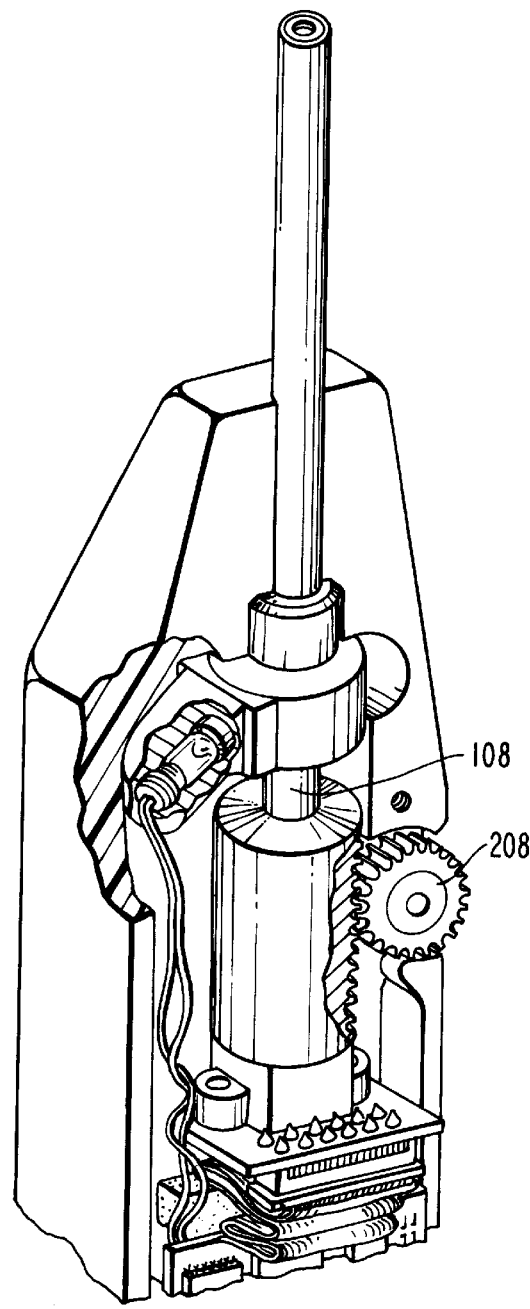
FIG. 11 is a partial view of the portable endoscopic camera of FIG. 10 with the camera coupler adjusted in the proximal direction, exposing the proximal end of the lens tube.

FIG. 10 demonstrates another embodiment of a portable endoscopic camera 220. Camera 220 is similar to camera 200. As shown in the embodiment of FIG. 10, however, the longitudinal portion 222 (shown in FIG. 4) of input port 110 parallel lens tube 32 is removed and lens fiber bundle 112 terminates in the angled portion 224 of input port 226 which is at an angle with respect to the longitudinal axis of lens tube 32. Thus, fiber bundle 112 terminates immediately after entering fiber light input port 226 at an angle from lens tube 32. Bulb 100 of lamp assembly 94 abuts the fiber bundle 112 directly after fiber bundle 112 exits lens tube 32 in this angled position, bringing bulb 100 closer to lens tube 32 and avoiding the travel of light through longitudinal portion 222. FIG. 11 is an example of portable endoscopic camera 220 of FIG. 10 adjusted by thumbwheel 208 such that camera coupler 90 is directed proximally along the longitudinal axis of lens tube 32.

To avoid the use of lubrication for moving parts, a highly polished type of housing 202 is preferred. Each of the housings may be water proof or water resistant, such as by disposing a rubber grommet or O-ring around the seals. In addition, water tight electrical adapters may be employed in conditions where water damage is likely, such as surgery or underwater procedures. In these procedures, a rubber or plastic seal is placed about the adapters. Focus wheel 208 or focus bridge 92 are removed and the housing surrounding them, such as slots 26 may be filled in for increased water tight or water proof capability. During operation, a set screw may be employed on the external surface of the housing to set the focus, the set screw communicating with a corresponding sprocket within the housing, the sprocket interlocking with tracks 210 on camera coupler 90 for sliding camera coupler 90.

K. The Interchangeable Probes

Figure 12:
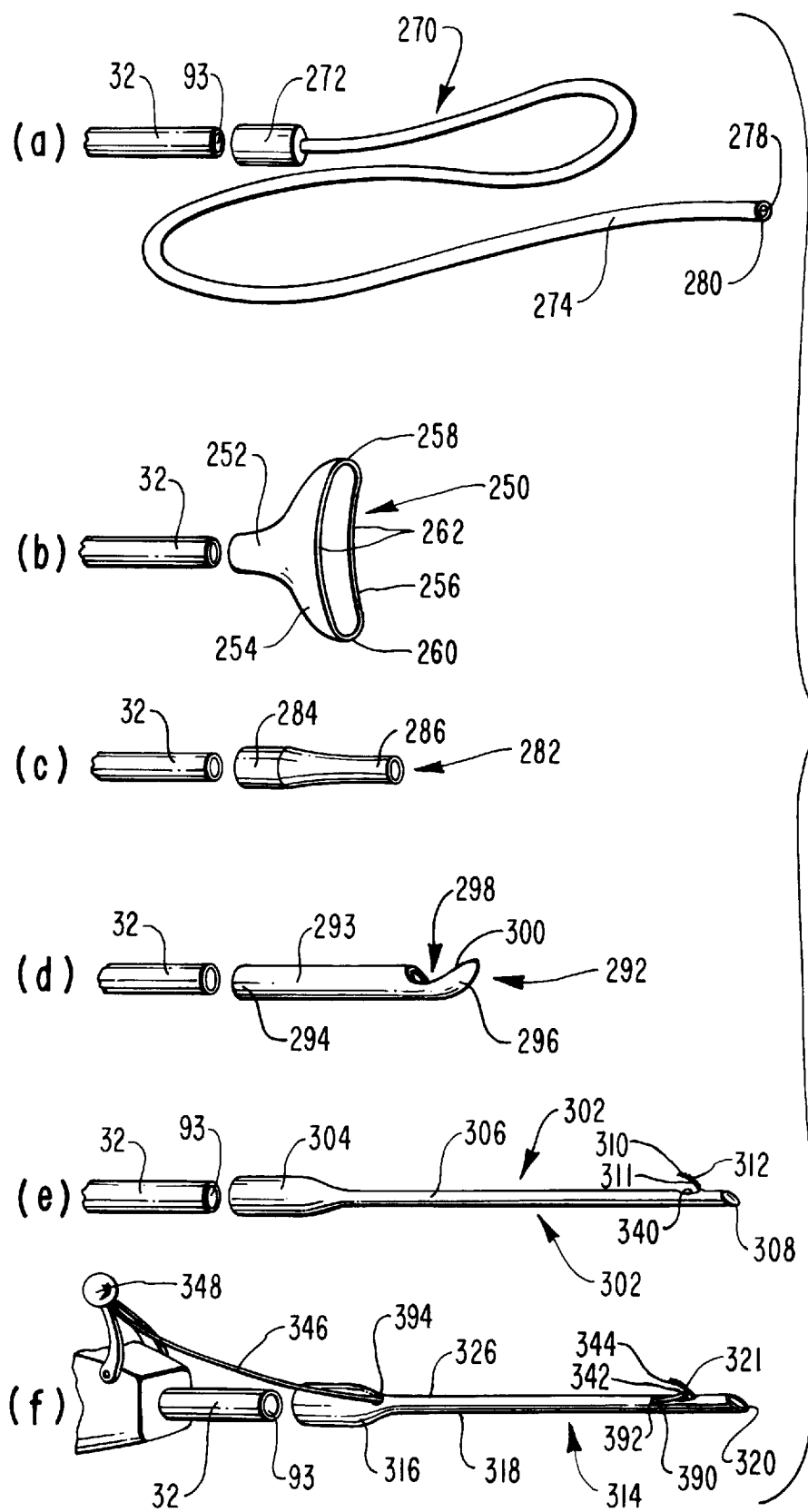
FIGS. 12a through 12h are perspective views of a variety of probes which are preferably placed directly on the lens tube of the various embodiments of portable endoscopic cameras disclosed herein.

As a further aspect of the present invention, portable endoscopic camera in each embodiment herein disclosed is highly versatile in that a variety of probe means may be optically coupled to the lens means, either directly to the distal end of the lens tube 32 or to a probe coupler 30 on lens tube 32, as shown in FIG. 1. The probe means disclosed in FIG. 12 are specifically designed to fit directly on lens tube 32. Thus, in the preferred embodiment, lens tube 32 has a universal design which mates with a variety of probes. When a different probe is needed a new coupler or camera is not required.

Probes may be secured to lens tube 32 in a variety of ways. In one embodiment the lens tube 32 has external threads which mate with internal threads within the necks of the probes. In another embodiment, a single thread on the probe mates with a single slit on lens tube 32 or a single slit on the probe mates with a single thread on lens tube 32. The probes may be made from stainless steel, plastic, aluminum or a variety of other materials known by those skilled in the art.

FIG. 12a demonstrates a fiber optic cable probe 270 for use in inspecting a variety of objects. Fiber optic cable probe 270 is designed for wrapping around a wall, for example, to view objects on the other side or for disposition into structures such as computer equipment, anatomical orifices, or in a variety of other places.

Fiber optic cable probe 270 is comprised of a neck 272 having an interior surface defining a passageway for placement of lens tube 32 therein. A fiber optic cable 274 extends distally from neck 272, a proximal end of fiber optic cable 326 preferably disposed against the distal end 93 of lens tube 32. A distal lens 278 is disposed at the distal end 280 of fiber optic cable 274. Thus, an image illuminated by fiber optic cable 274 and viewed through distal lens 278 is translated through fiber optic cable 326 to lens tube 32. While fiber optic cable 274 may be designed to have varying lengths, it is preferably designed to be approximately three feet long, to reach around various objects.

FIG. 12b demonstrates an eye speculum 250 for use in inspecting a variety of objects, such as the eye and related anatomy. For example, eye speculum 250 may be employed in photographing stages of cataract maturation and for use in plastic surgery relating to the eyelids. Eye speculum 250 is contoured similar to an eye wash cup for rinsing the eye.

Eye speculum 250 is comprised of a neck 252 having an interior surface defining a passageway for placement of lens tube 32 therein. A speculum body 254 integrally attached to speculum neck 252 extends outwardly and distally from neck 252. Speculum body 254 is contoured at a distal end 256 in an approximate oval shape, having a rounded upper edge 258, a rounded lower edge 260 and opposing side edges 262 which recess proximally with respect to upper edge 258 and lower edge 260 such that the speculum 250 is placed about the eye for inspection of the eye when coupled to lens tube 32. The distance between upper edge 258 and lower edge 260 is greater than the distance between opposing side edges 262.

FIG. 12c demonstrates an otoscope speculum 282 for use in inspecting a variety of objects. Otoscope speculum 282 is comprised of a neck 284 having an interior surface defining a passageway for placement of lens tube 32 therein. A speculum body 286 integrally attached to speculum neck 266 extends inwardly and distally from neck 284.

In another embodiment of otoscope speculum 282, it is possible to flush an ear or other cavity while looking into the cavity, employing a means for flushing, the flushing means attached to housing 12, lens tube 32 or otoscope 282. Such flushing means includes, for example, a tube which is parallel lens tube 32 and the longitudinal axis of otoscope speculum 282. A syringe disposed at a proximal end of the tube releases flushing fluid into the tube. The tube has an opening at a distal end near the distal end of otoscope 282 for the release of fluid into the cavity during the observation.

Figure 12G:
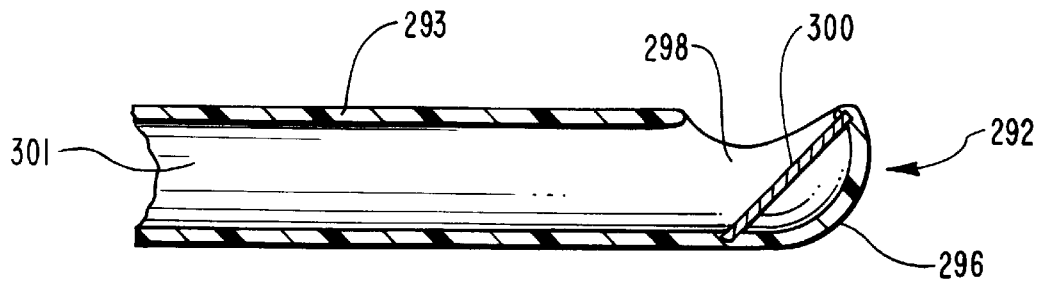

FIGS. 12d and 12g demonstrate in a perspective view and in cross section, respectively, a mirror speculum 292 for use in inspecting a variety of objects, such as a tooth. For example, mirror speculum 292 can be employed to inspect cracks in teeth or gum disease. Mirror speculum 292 is comprised of a tubular housing 293 having an interior surface 301 defining a passageway. Tubular housing 293 is configured for placement of lens tube 32 therein. A distal end 296 is closed. Tubular housing 293 includes an aperture 298 proximal to distal end 296. Aperture 298 is configured for reception of an object such as a tooth. A mirror 300 is disposed in the passageway within housing 293 adjacent aperture 298 and is oriented to reflect the image of the received object into lens tube 32. Preferably, lens tube 32 is disposed within housing 293 such that distal end 93 of lens tube 32 is approximately ½ inch from mirror 300.

FIG. 12e demonstrates a first biopsy speculum 302 for use in inspecting a variety of objects and for taking a biopsy of an inspected object without making an incision. First biopsy speculum 302 is comprised of a neck 304 having an interior surface defining a passageway for placement of lens tube 32 therein. A speculum body 306 integrally attached to speculum neck 304 extends inwardly and distally from neck 304. Speculum body 306 is in the shape of a needle and contains a fiber optic cable, preferably a single fiber optic strand. A proximal portion of the fiber optic cable is preferably disposed against the distal end 93 of lens tube 32. The fiber optic cable includes a lens at distal end 308 for viewing the area to be biopsied.

A spoon 310 having a serrated distal face 312 is disposed near distal tip 308 for taking a biopsy sample while biopsy speculum body 306 is disposed within the area to be biopsied. Thus it is possible for the practitioner to view the area, through lens tube 32 and take a biopsy with spoon 310.

As spoon 310 scrapes biopsied material, the material accumulates in groove 340. At least one side 311 of spoon 310 is sharpened such that upon twisting speculum 302 the sharpened side 311 makes an incision. Spoon 310 is then employed to scrape and retrieve the incised portion.

FIG. 12f demonstrates a second biopsy speculum 314 for use in inspecting a variety of objects and for taking a biopsy of an inspected object without making an incision. Second biopsy speculum 314 is comprised of a neck 316 having an interior surface defining a passageway for placement of lens tube 32 therein. A speculum body 318 integrally attached to speculum neck 316 extends inwardly and distally from neck 316. Speculum body 318 is in the shape of a needle and contains a fiber optic cable, preferably a single fiber optic strand. A proximal portion of the fiber optic cable is preferably disposed against the distal end 93 of lens tube 32. The fiber optic cable includes a lens at distal end 320 for viewing the area to be biopsied.

A spoon 321, possibly having a serrated distal end 320, is pivotally mounted on a pivot pin, for example, within speculum body 318 near distal end 320, for taking a biopsy sample while biopsy speculum body 318 is disposed within the area to be biopsied. Thus it is possible for the practitioner to view the area, through lens tube 32 and take a biopsy with spoon 310.

As spoon 321 scrapes biopsied material, the material accumulates in groove 342. At least one side 344 of spoon 321 is sharpened such that upon twisting speculum 314 the sharpened side 344 makes an incision. Spoon 321 is then employed to scrape and retrieve the incised portion.

Second biopsy speculum body 318 further comprises a tube 390 disposed parallel to the fiber optic cable for disposition of a wire 346 therethrough. Wire 346 or other means for directing spoon 321 is disposed within tube 390. Wire 346 exits a distal end 392 of the tube 390 and at a distal end of wire 346 attaches to spoon 321 for pivoting spoon 321 in a proximal or distal direction. Spoon 321 is preferably pushed distally against body 318 as speculum 314 is disposed into the body or other cavity, minimizing the interference of spoon 321 against the skin. Wire 346 exits a proximal end 394 of tube 390 and is attached at a proximal end of wire 346 to a lever 348 mounted on neck 316, lens tube 32, or on a distal portion of the camera housing. Wire 346 assists in orienting spoon 321 in a desired position.

Figure 12H:
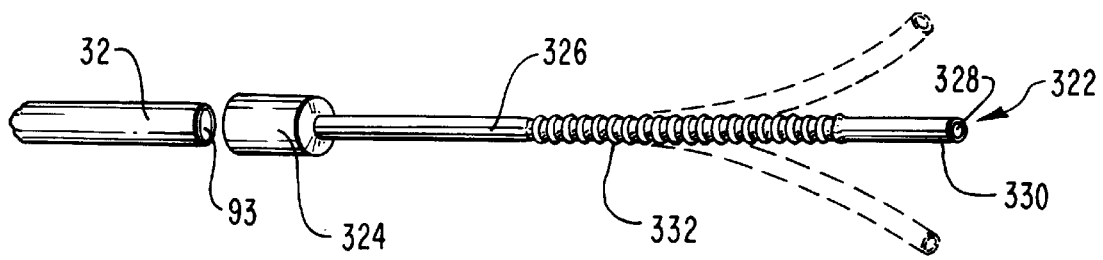

FIG. 12h demonstrates a memory probe 322. Memory probe 322 is selectively shaped and retains its selective shape for use in inspecting a variety of objects. Memory probe 322 is designed for bending into a particular shape and for retaining the shape. Thus, the probe 322 can be wrapped around a wall or other structure and used in its originally selected shape.

Memory probe 322 is comprised of a neck 324 having an interior surface defining a passageway for placement of lens tube 32 therein. A fiber optic cable 326 extends distally from neck 324, a proximal end of fiber optic cable 326 preferably disposed against the distal end 93 of lens tube 32. A distal lens 328 is disposed at the distal end 330 of memory probe 322. Thus, an image illuminated by memory probe 322 and viewed through distal lens 328 is translated through fiber optic cable 326 into lens tube 32. Fiber optic cable 326 is preferably approximately one foot in length.

In order to create the memory dynamic, a memory plastic having accordion-shaped ribs 332, such as used with memory plastic flexible drinking straws, coats the outer surface of fiber optic cable 326. Preferably a non-ABS plastic is employed.

FIG. 13 demonstrates a coupler 352, which is an example of a means for coupling the lens means to a funnel-shaped probe 350. Funnel shaped probes are particularly useful for the inspection of the ear. Coupler 352 includes a neck 354 having an interior surface defining a passageway for placement of lens tube 32 therein. A coupler body 356 integrally attached to neck 354 extends outwardly and distally from neck 354 in a funnel shape. Coupler body 356 is contoured at a distal end 358 in a circular shape. A clamp, such as a circular-shaped clamp or a C-shaped "C" clamp 360 made of flexible plastic or rubber extends from the distal end 358 of coupler body 356 and is disposed about funnel probe 350 for retaining the distal end 358 of coupler 352 in an abutting relationship with the proximal end 359 of funnel probe 350. In one embodiment, distal end 93 of lens tube 32 is disposed against the proximal end of a fiber optic cable disposed within funnel-shaped probe 350 in an abutting relationship.

FIGS. 14 and 15 demonstrate microscope coupler 361. Microscope coupler 361 is an example of a means coupled to a microscope 362 for translating an image within the microscope 362 into the lens means of portable endoscopic camera 10. Microscope coupler 361 includes a neck 364 having an interior surface defining a passageway for placement of lens tube 32 therein. A coupler body 366 integrally attached to neck 364 extends outwardly and distally from neck 364. Coupler body 368 includes dual ring shaped ports 370 configured to receive the microscopic eye-pieces 372. A C-clamp 378 is used, for example, to retain eye-pieces 372 within ports 370.

As shown in cross section in FIG. 15, the image viewed within each microscopic eye-piece 372 is projected to a corresponding side mirror 374 within microscope coupler 361. Each side mirror 374 reflects the image onto a central mirror 376, which reflects the combined image to lens tube 32.

The advantage provided by microscope coupler 361 is that it allows a practitioner to add additional magnification to a microscoped image. In addition, the practitioner is able to transmit the image through signal unit 70, for example, to a wall mounted monitor for view of the image by a larger number of practitioners.

In addition to the variety of possible uses of the disclosed endoscopic camera, various modifications increase the potential uses for the invention. For example, it is possible to remove lens fiber module 88 and place the apparatus in a remote control activated device, such as model air plane or model car. A full size lens is mounted on the camera, for example. A monitor, such as a liquid display monitor, is then mounted on a remote control operating device. Thus, the operator could view the flight path of the airplane, for example in the display monitor. In another embodiment it is possible to remove lens fiber module 88 and employ the remaining hand held unit to see around corners or within or through walls, for example. In another embodiment, it is possible to employ the battery operated device as a security camera, with or without lens fiber module 88.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A portable, hand-held apparatus for producing video images of an object, the portable, hand held apparatus, comprising:

light source means for producing light for illumination of the object;

video imaging means for generating a video single of the object;

lens means having a distal end and a proximal end, said lens means being optically coupled at its proximal end to the light source means for translating light from the light source means to the distal end of the lens means and for emitting the translated light from the distal end of the lens means so as to illuminate the object when the distal end of the lens means is positioned adjacent the object, said lens means also being optically coupled at its proximal end to the video imaging means for translating an image of said object from the distal end of said lens means to the video imaging means; and power supply means electrically coupled to, and for supplying electrical power to, said light source means and said video imaging means, wherein the lens means includes a fiber bundle, the light source means includes a bulb, and the bulb is in an abutting relationship with the fiber bundle.

2. An apparatus as in claim 1 further comprising display means, electrically coupled to said video imaging means, for displaying video images of the object.

3. An apparatus as in claim 1 further comprising:

transmitter means, electrically coupled to the video imaging means, for transmitting video signals generated by said video imaging means;

receiver means for receiving the video signals transmitted by said transmitter means; and display means, electrically coupled to said receiver means, for displaying video images of the object.

4. An apparatus as in claim 1, further comprising hand-held means for housing the light source means, video imaging means, lens means, and power supply means.

5. An apparatus as in claim 4, wherein the lens means comprises a collar;

the hand-held housing means includes an interior surface;

the interior surface of the hand-held housing means defines a channel configured for reception of the light source means and the collar; and wherein the collar is disposed about a distal portion of the light source means.

6. An apparatus as in claim 1, further comprising means for retaining the lens means in an abutting relationship with the light source means.

7. An apparatus as in claim 1, further comprising a probe optically coupled to the distal end of the lens means.

8. An apparatus as in claim 7 wherein the probe comprises a fiber optic cable.

9. An apparatus as in claim 8 wherein the fiber optic cable is rigid.

10. An apparatus as in claim 8 wherein the fiber optic cable is flexible.

11. An apparatus as in claim 7 wherein the probe comprises a speculum.

12. An apparatus as in claim 11 wherein the probe comprises an otoscope speculum.

13. An apparatus as in claim 7 wherein the probe is selectively shaped and retains its selective shape.

14. An apparatus as in claim 7 wherein the probe includes an aperture configured to receive the object and wherein a mirror is disposed within the aperture for reflecting the image of the object into the lens means.

15. An apparatus as in claim 7 wherein the probe is configured to fit about an eye.

16. An apparatus as in claim 1, further comprising coupling means for coupling the lens means to a funnel-shaped probe.

17. An apparatus as in claim 1 further comprising intensity adjustment means, electrically coupled to said light source means, for varying the intensity of the light produced by said light source means.

18. An apparatus as in claim 1, wherein the video imaging means comprises:
   a sensor array coupled to the proximal end of said lens means; and
   conversion means, electrically coupled to said sensor array, for converting images translated by the lens means and impinging upon said sensor array into video signals and for outputting the converted video signals.

19. An apparatus as in claim 18 wherein the conversion means produces an S-VHS video signal output.

20. An apparatus as in claim 18 wherein the conversion means produces a composite video signal output.

21. An apparatus as in claim 18 wherein the conversion means produces both an S-VHS video signal output and a composite video signal output.

22. An apparatus as in claim 18 further comprising focusing means, coupled to said sensor array, for focusing the translated image of the object onto the sensor array by adjusting the distance separating the sensor array and the proximal end of the lens means.

23. An apparatus as in claim 18, wherein
   the lens means comprises a lens tube; and wherein
   a means for optically coupling the lens tube to the video imaging means optically couples a proximal end of the lens tube to the video imaging means, the means for optically coupling the lens tube to the video imaging means comprising a coupling housing having a tubular interior surface, a distal end of the tubular interior surface disposed about a proximal end of the lens tube and a proximal end of the tubular interior surface disposed about the sensor array.

24. An apparatus as in claim 18, further comprising means for focusing the translated image of the object onto the sensor array by adjusting the distance separating the sensor array and the proximal end of the lens means and for maintaining the longitudinal axis of the lens means.

25. A portable, hand-held apparatus for producing video images of an object, the apparatus comprising:
   light source means for producing light for illumination of the object;
   video camera means for generating a video signal of the object, said video camera means comprising a CCD sensor array, and conversion means electrically coupled to said CCD sensor array for converting images impinging upon said CCD sensor array into video signals, and for outputting the converted video signals;
   lens means having a distal end and a proximal end, said lens means being optically coupled at its proximal end to the light source means for translating light from the light source means to the distal end of the lens means and for emitting the translated light from the distal end of the lens means so as to illuminate the object when the distal end of the lens means is positioned adjacent the object, said lens means also being optically coupled at its proximal end to the video camera means for translating an image of said object from the distal end of said lens means to the CCD sensor array; and
   power supply means electrically coupled to, and for supplying electrical power to, said light source means, and said video camera means, wherein
   the lens means includes a fiber bundle;
   the light source means includes a bulb; and
   the bulb is disposed in an abutting relationship with the fiber bundle.

26. An apparatus as in claim 25, further comprising hand-held means for housing the light source means, video imaging means, lens means, and power supply means.

27. An apparatus as in claim 26, wherein
   the lens means comprises a collar;
   the hand-held housing means includes an interior surface;
   the interior surface of the hand-held housing means defines a channel configured for reception of the light source means and the collar; and wherein
   the collar is disposed about a distal portion of the light source means.

28. An apparatus in claim 25, wherein:
   the bulb has the same diameter as the diameter of the fiber bundle.

29. An apparatus as in claim 25, further comprising:
   display means, electrically coupled to said video imaging means, for displaying video images of the object; and
   hand-held means for housing the light source means, video camera means, lens means, display means, and power supply means, wherein the display means is mounted to the hand-held housing means;
   such that the apparatus is self-contained.

30. A portable, hand-held apparatus for producing video images of an object comprising:
   light source means for producing light for illumination of the object;
   video camera means for generating a video signal of the object, said video camera means comprising a CCD sensor array, and conversion means electrically coupled to said CCD sensor array for converting images impinging upon said CCD sensor array into video signals, and for outputting the converted video signals;
   lens means having a distal end and a proximal end, said lens means being optically coupled at its proximal end to the light source means for translating light from the light source means to the distal end of the lens means and for emitting the translated light from the distal end of the lens means so as to illuminate the object when the distal end of the lens means is positioned adjacent the object, said lens means also being optically coupled at its proximal end to the video camera means for translating an image of said object from the distal end of said lens means to the CCD sensor array;
   video monitor display means, electrically coupled to said video camera means, for displaying video images of the object; and power supply means electrically coupled to, and for supplying electrical power to, said light source means, said video camera means, and said video monitor display means;

wherein the light source means is disposed directly against the lens means in an abutting relationship and wherein:

the light source means includes a proximal portion, a distal portion, and an intermediate portion intermediate the proximal and distal portions;

the lens means comprises a cylindrical collar, the cylindrical collar disposed about the distal portion of the light source means; and the apparatus further comprises a strap and a lid; wherein the strap is disposed under the collar and the intermediate portion of the light source means; and the lid is disposed above the collar and the intermediate portion of the light source means; such that light from the light source means is focused into the lens means.

31. An apparatus as in claim 30, further comprising means for focusing the translated image of the object onto the sensor array by adjusting the distance separating the sensor array and the proximal end of the lens means and for maintaining the longitudinal axis of the lens means.

32. An apparatus as in claim 31, wherein the means for focusing the translated image of the object onto the sensor array by adjusting the distance separating the sensor array and the proximal end of the lens means and for maintaining the longitudinal axis of the lens means comprises a focus bridge.

33. An apparatus as in claim 31, wherein:

the lens means includes an exterior surface, the exterior surface having ridges disposed thereon; and wherein the means for focusing the translated image of the object onto the sensor array by adjusting the distance separating the sensor array and the proximal end of the lens means and for maintaining the longitudinal axis of the lens means comprises a thumb wheel configured to engage the ridges.

34. An apparatus as in claim 30, further comprising hand-held means for housing the light source means, video camera means, lens means, video monitor display means, and power supply means, wherein the video monitor display means is mounted to the hand-held housing means, such that the apparatus is self-contained.

35. An apparatus as in claim 30, wherein the light source means comprises an incandescent lamp having a bulb and a base;

the distal portion of the light source means comprising the bulb; and wherein a socket is configured to house the base, the socket having socket feet;

the proximal portion of the light source means comprising the socket feet.

36. A portable, hand-held apparatus for producing video images of an object, the portable, hand held apparatus, comprising:

light source means for producing light for illumination of the object;

video imaging means for generating a video signal of the object;

lens means having a distal end and a proximal end, said lens means being optically coupled at its proximal end to the light source means for translating light from the light source means to the distal end of the lens means and for emitting the translated light from the distal end of the lens means so as to illuminate the object when the distal end of the lens means is positioned adjacent the object, said lens means also being optically coupled at its proximal end to the video imaging means for translating an image of said object from the distal end of said lens means to the video imaging means;

power supply means electrically coupled to, and for supplying electrical power to, said light source means and said video imaging means; and means coupled to a microscope for translating an image within the microscope into the lens means.

37. A portable, hand-held apparatus for producing video images of an object, the apparatus comprising:

light source means for producing light for illumination of the object;

video camera means for generating a video signal of the object, said video camera means comprising a CCD sensor array, and conversion means electrically coupled to said CCD sensor array for converting images impinging upon said CCD sensor array into video signals, and for outputting the converted video signals;

lens means having a distal end and a proximal end, said lens means being optically coupled at its proximal end to the light source means for translating light from the light source means to the distal end of the lens means and for emitting the translated light from the distal end of the lens means so as to illuminate the object when the distal end of the lens means is positioned adjacent the object, said lens means also being optically coupled at its proximal end to the video camera means for translating an image of said object from the distal end of said lens means to the CCD sensor array;

power supply means electrically coupled to, and for supplying electrical power to, said light source means, and said video camera means;

wherein the lens means comprises a lens tube, and a means for optically coupling the lens tube to the video imaging means optically couples a proximal end of the lens tube to the video imaging means, the means for optically coupling the lens tube to the video imaging means comprising a coupling housing having a tubular interior surface, a distal end of the tubular interior surface disposed about a proximal end of the lens tube and a proximal end of the tubular interior surface disposed about the CCD sensor array; and further comprising focusing means, configured to receive the means for optically coupling the lens tube to the video imaging means, for focusing the translated image of the object onto the CCD sensor array by adjusting the distance separating the CCD sensor array and the proximal end of the lens tube, the focusing means comprising:

a beam having a horizontal axis; and a pair of support members extending vertically upward with respect to the horizontal axis of the beam from opposing ends of the beam, the beam and the pair of support members defining a U-shaped channel, each support member further including a flange extending outwardly with respect to the U-shaped channel, each flange parallel to the horizontal axis of the beam.

* * * * *

UNITED STATES PATENT AND TRADEMARK OFFICE
CERTIFICATE OF CORRECTION

PATENT NO. : 5,879,289

DATED : March 9, 1999

INVENTOR(S) : Don Yarush, Martin G. Sosa, Gary Handelin

It is certified that error appears in the above-identified patent and that said Letters Patent are hereby corrected as shown below:

Cover Page, Appl. No., left column, change "680,174" to --08/680,174--

Cover Page, References Cited, left column, line 19, change "Giraham" to -- Graham--

Cover Page, Other Publications, line 4, change "Cudal" to --Cuda--

Col. 6, line 53, after "is a" change "222" to --222--

Col. 7, line 28, after "board" change "90" to --80--

Col. 8, line 47, before "is" insert "10"

Col. 10, line 31, after "12" change "defames" to --defines--

Col. 10, line 36, after "is" change "defames" to --defines--

Col. 10, line 49, after "assembly" change "66" to --67--

Col. 12, line 3, after "156." insert --Alternatively, channel 140 is configured such that upper edges 155 are disposed upon ridges 156.--

Col. 12, line 63, before "171" change "Lid" to --lid--

Col. 14, line 13, after "lamp" change "assemble" to --assembly--

Col. 14, line 19, after "require" change "a" to --an--

Col. 15, line 59, after "contents" insert --of--

UNITED STATES PATENT AND TRADEMARK OFFICE
CERTIFICATE OF CORRECTION

PATENT NO. : 5,879,289

DATED : March 9, 1999

INVENTOR(S) : Don Yarush, Martin G. Sosa, Gary Handelin

It is certified that error appears in the above-identified patent and that said Letters Patent are hereby corrected as shown below:

Col. 20, line 18, after "video" change "single" to --signal--

Signed and Sealed this

Twenty-ninth Day of May, 2001

Attest:

NICHOLAS P. GODICI

Attesting Officer

Acting Director of the United States Patent and Trademark Office